United States Patent
Kong et al.

(10) Patent No.: US 12,201,730 B2
(45) Date of Patent: Jan. 21, 2025

(54) CATALYTIC MICROGELATORS FOR DECOUPLED CONTROL OF GELATION RATE AND RIGIDITY OF BIOLOGICAL GELS

(71) Applicant: THE BOARD OF TRUSTEES OF THE UNIVERSITY OF ILLINOIS, Urbana, IL (US)

(72) Inventors: Hyunjoon Kong, Champaign, IL (US); Yu-Tong Hong, Urbana, IL (US); Yongbeom Seo, Woodbury, MN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 417 days.

(21) Appl. No.: 17/221,203

(22) Filed: Apr. 2, 2021

(65) Prior Publication Data
US 2021/0308064 A1  Oct. 7, 2021

Related U.S. Application Data

(60) Provisional application No. 63/003,925, filed on Apr. 2, 2020.

(51) Int. Cl.
| | |
|---|---|
| A61K 38/48 | (2006.01) |
| A61K 9/06 | (2006.01) |
| A61K 9/50 | (2006.01) |
| A61K 38/36 | (2006.01) |
| A61K 47/02 | (2006.01) |
| A61P 7/04 | (2006.01) |
| B01J 23/34 | (2006.01) |
| B01J 31/06 | (2006.01) |
| B01J 35/50 | (2024.01) |
| B01J 37/00 | (2006.01) |

(52) U.S. Cl.
CPC ............. *A61K 9/5031* (2013.01); *A61K 9/06* (2013.01); *A61K 38/363* (2013.01); *A61K 38/4833* (2013.01); *A61K 47/02* (2013.01); *A61P 7/04* (2018.01); *B01J 23/34* (2013.01); *B01J 31/06* (2013.01); *B01J 35/50* (2024.01); *B01J 37/0072* (2013.01)

(58) Field of Classification Search
CPC ...... A61K 9/5031; A61K 9/06; A61K 38/363; A61K 38/4833; A61K 47/02; A61P 7/04; B01J 23/34; B01J 31/06; B01J 35/026; B01J 37/0072; B01J 31/061; B01J 31/003; B01J 31/063; B01J 31/32; B01J 35/0006; B01J 35/0013; B01J 37/0009; B01J 37/343

See application file for complete search history.

(56) References Cited

U.S. PATENT DOCUMENTS

| | | |
|---|---|---|
| 9,533,073 B1 | 1/2017 | Kong et al. |
| 2009/0232876 A1* | 9/2009 | Montes ............... A61K 9/0007 424/94.4 |

FOREIGN PATENT DOCUMENTS

| | | | | |
|---|---|---|---|---|
| CA | 2801118 A1 * | 12/2011 | ......... | A61K 38/4833 |
| WO | WO-2013123492 A2 * | 8/2013 | ............. | A61K 38/28 |

OTHER PUBLICATIONS

Teo et al., Biomaterials 201 (2019) 1-15. (Year: 2019).*
Lopez et al., J. Thrombosis and Haemostasis, 5:1283-1291 (2007). (Year: 2007).*
Shabanova et al., Scientific Reports (2018) 8:233, 1-10 (Year: 2018).*
Jeong et al, "'Living' Microvascular Stamp for Patterning of Functional Neovessels; Orchestrated Control of Matrix Property and Geometry", Advanced Materials, vol. 24, pp. 58-63, (2012).
Lee et al, "Glacier Moraine Formulation-Mimicking Colloidal Particle Assembly in Microchanelled, Bioactive Hydrogel for Guided Vascular Network Construction", Advanced Healthcare Materials, pp. 1-7, (2014).
Levi et al, "Fibriongen-coated albumin microcapsules reduce bleeding in severely thrombocytopenia rabbits", Nature Medicine, vol. 5, No. 1, pp. 107-111, Jan. 1999.
Melhem et al, "3D Printed Stem-Cell-Laden, Microchanneled Hydrogel Patch for the Enhanced Release of Cell-Secreting Factors and Treatment of Myocardial Infarctions", ACS Biomaterials Science & Engineering, 8 pages, (2016).
Nishiya et al, "Reconstruction of adhesive properties of human platelets in liposomes carrying both recombinant glycoproteins Ia/IIa and Ibα under flow conditions: specific synergy of receptor-ligand interactions", Blood, vol. 100, No. 1, pp. 136-142, Jul. 1, 2002.

* cited by examiner

*Primary Examiner* — Robert S Cabral
(74) *Attorney, Agent, or Firm* — Lathrop GPM LLP; Lisa Hillman

(57) ABSTRACT

Provided herein are stimulus-responsive polymer microgelator particles that can activate fibrin fiber formation from their surfaces by actively ejecting thrombin to form an interconnected fibrin network with an increased elastic modulus and desirable microstructure. The use of the microgelators enables the decoupling of gelation rate and gel rigidity.

22 Claims, 20 Drawing Sheets

Blood clot formation triggered by thrombin

CATALYTIC MICROGELATORS FOR DECOUPLED CONTROL OF GELATION RATE AND RIGIDITY OF BIOLOGICAL GELS

PRIORITY

This application claims the benefit of U.S. Ser. No. 63/003,925, filed on Apr. 2, 2020, which is incorporated by reference in its entirety herein.

STATEMENT REGARDING FEDERALLY SPONSORED RESEARCH AND DEVELOPMENT

This invention was made with government support under grant R21 HL131469, awarded by the National Institutes of Health and STC-EBICS Grant CBET-0939511 and CBET-1553137 awarded by the National Science Foundation. The Government has certain rights in the invention.

BACKGROUND

Fibrinogen in the blood forms a fibrin gel that can control bleeding and heal wounds. In general, platelets activated in injuries initiate a coagulation cascade that leads to thrombin formation. Thrombin then converts water-soluble fibrinogen to insoluble fibrin by cleaving the fibrinopeptide at the center domain. The resulting active sites react with each other to form a three-dimensional fibrin fiber network. The gel is then further stabilized through chemical crosslinking reaction by factor XIII. Fibrin associated with platelets forms blood clots in wounded tissue and acts as a provisional matrix that supports cellular activities essential for wound healing and tissue regeneration. Fibrous networks of fibrin gels are advantageous to transporting biomolecules while sequestering cells. Therefore, fibrin gels prepared using isolated or recombinant fibrinogen have also been used for three-dimensional cell cultures, tissue glues, and molecular/cell therapies.

It is common to assemble fibrin gels by mixing the fibrinogen solution with thrombin molecules in a powder or solution form. The quick gelation process leads to difficulties in handling the gel for cell encapsulation and implantation. Several approaches exist to control gelation rate, including alteration of the concentrations of fibrinogen, thrombin, calcium chloride, and Factor XIII. For instance, decreasing the concentration of thrombin slows the gelation, thus providing users with an increased time window for delivery of the gel. However, the resulting gel presents a significant change in microstructure, where the fiber diameter increases and the branching points decrease. In addition, decreasing thrombin concentration increases the elastic modulus of the fibrin gel. However, a further decrease of the thrombin concentration below 0.25 NIHU/ml softens the gel. Overall, it would be desirable to have a tool that provides a broader window for control of gelation while minimally altering the microstructure and mechanical properties of the fibrin gel. A small window for gelation makes it difficult to handle the gels for desired preparation and transport.

Furthermore, hemostatic particles can be used treat a severe injury that is not amenable to hemostasis. These particles reproduce the biological function of natural platelets that adhere to the bleeding site and aggregate. For instance, liposomes were decorated with Glycoprotein Ia-IIa that adhere to the Von Willebrand factor (vWF) or collagen to promote adhesion to a bleeding site. Nishiya et al., *Blood* 2002, 100, 136-142. To reproduce aggregation effect of the platelets, fibrinogen or fibrinogen-binding peptide molecules have been incorporated into the surface of microparticles. Levi et al., *Nat. Med.* 1999, 5, 107-111. However, bleeding often washes out these coagulation factors, including thrombin, thus limiting fibrin network formation. Compositions and methods are needed for improving the quality of current hemostatic particles by promoting particle-fiber connection and reinforcing blood clots.

SUMMARY

An embodiment provides composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer. The catalyst for the decomposition of hydrogen peroxide can be (1) manganese oxide ($MnO_2$), platinum (Pt), CuO (copper II oxide), or zinc peroxide ($ZnO_2$) particles or nanosheets, or (2) catalase. The composition can be lyophilized. The polymer can be a biodegradable polymer. One mg of the composition can comprise about 1 µg to about 20 µg of catalyst for the decomposition of $H_2O_2$ and about 25 ng to about 150 ng of thrombin.

Another embodiment provides a method of clotting blood or a blood product containing fibrinogen. The method comprises:
(a) adding $H_2O_2$ to a composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer to form a mixture and adding the mixture to the blood or blood product;
(b) adding $H_2O_2$ to the blood or blood product to form a mixture and adding a composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer to the mixture; or
(c) adding $H_2O_2$ and a composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer to the blood or blood product to form a mixture. Fibrinogen can additionally be added to the blood or blood product or to any of the mixtures of (a), (b), or (c).

Yet another embodiment provides a method of promoting blood clotting in a subject comprising adding $H_2O_2$ to a composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer to form a mixture and then administering an effective amount of the mixture to the subject. Fibrinogen can be added to the mixture before administering the mixture to the subject. The subject can have a coagulopathic condition or tissue defect and the method can be effective for treating the coagulopathic condition or tissue defect in the subject. The tissue defect can be an external wound, an internal wound, an ulcer, a burn, a natural defect, a surgical incision, or any combination thereof. The tissue defect can be caused by traumatic injury, disease, infection, surgical intervention, natural causes, or any combinations thereof.

Even another embodiment provides a method of making a gel comprising contacting a composition comprising a catalyst for the decomposition of hydrogen peroxide ($H_2O_2$) and thrombin, wherein the catalyst for the decomposition of hydrogen peroxide ($H_2O_2$) and thrombin are encapsulated within a polymer with a fibrinogen solution or powder and $H_2O_2$ to form a mixture and allowing the mixture to form a gel. The fibrinogen can be present at about 0.5 mg/ml to about 5.0 mg/ml in the fibrinogen solution or powder and the $H_2O_2$ can be present at about 0.1 mM to about 0.6 mM. One or more types of cells can be added to the mixture so that the cells are present within the gel. The cells can be endothelial cells, fibroblast cells, tissue specific cells, or a combination thereof. The endothelial cells can be adult vein endothelial cells, adult artery endothelial cells, embryonic stem cell-derived endothelial cells, iPS-derived endothelial cells, umbilical vein endothelial cells, umbilical artery endothelial cells, endothelial progenitor cells derived from bone marrow, endothelial progenitor cells derived from cord blood, endothelial progenitor cells derived from peripheral blood, endothelial progenitor cells derived from adipose tissues, or combinations thereof. The umbilical vein endothelial cells can be human umbilical vein endothelial cells (HUVEC). The fibroblast cells can be human foreskin fibroblasts, human embryonic fibroblasts, mouse embryonic fibroblasts, skin fibroblast cells, vascular fibroblast cells, myofibroblasts, smooth muscle cells, mesenchymal stem cells (MSCs)-derived fibroblast cells, or combinations thereof. The tissue-specific cells can be muscle cells, pancreatic beta cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, stem cell, iPS cell derived tissue specific cells, or a combination thereof. The tissue specific cells can be myoblasts, pancreatic beta-islet cells, cardiomyocytes, liver cells, lung cells, neural cells, bone cells, kidney cells, or combinations thereof.

Another embodiment provides a method of making a catalytic microgelator particle. The method comprises:
(a) adding thrombin to a suspension of an $H_2O_2$ decomposition catalyst to form an internal aqueous phase mixture;
(b) adding the internal aqueous phase mixture to an organic phase comprising a polymer in a solvent and mixing to form a first emulsion;
(c) adding the first emulsion to an external aqueous phase solution comprising a water soluble polymer and mixing to prepare a second emulsion; and
(d) collecting the resulting catalytic microgelator particles.

Therefore, provided herein are stimulus-responsive polymer catalytic microgelator particles that can activate fibrin fiber formation from their surfaces by actively ejecting thrombin to form an interconnected fibrin network with an increased elastic modulus and desirable microstructure. The use of the microgelators enables the decoupling of gelation rate and gel rigidity

$$n_{O_2} = \frac{1}{2} \times \text{(initial } H_2O_2 \text{ concentration} - \text{final } H_2O_2 \text{ concentration)} \times H_2O_2 \text{ volume}$$

Figure 15:
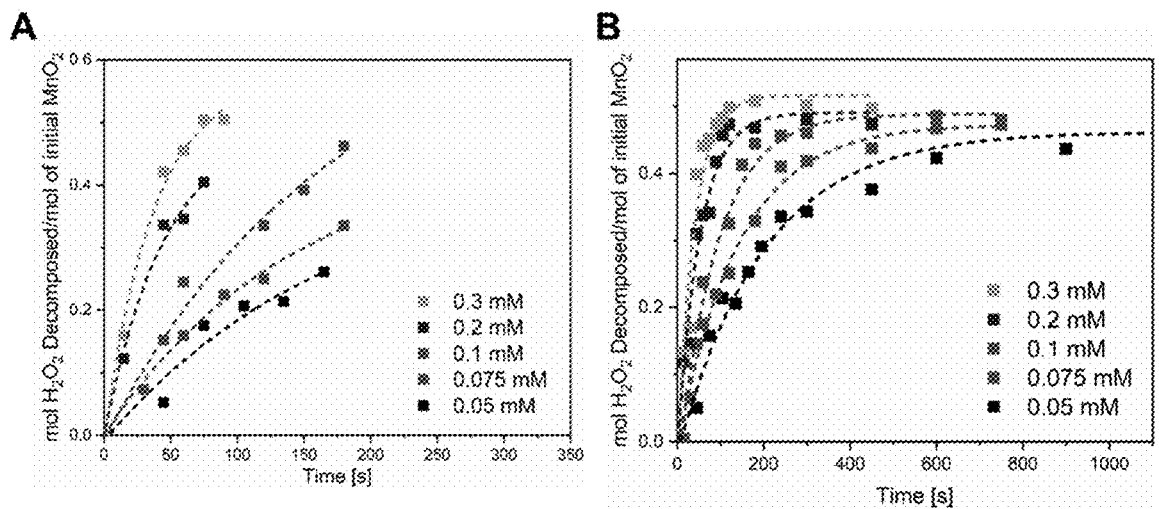

FIG. 15 shows $H_2O_2$ decomposition curve under varying initial $H_2O_2$ concentration. $H_2O_2$ decomposition curves attained by adding (A) $MnO_2$ nanosheets and (B) lyophilized PLGA/$MnO_2$ particles into media with varied $H_2O_2$ concentrations noted in each figure. Dash lines are for visual guide.

Figure 16:
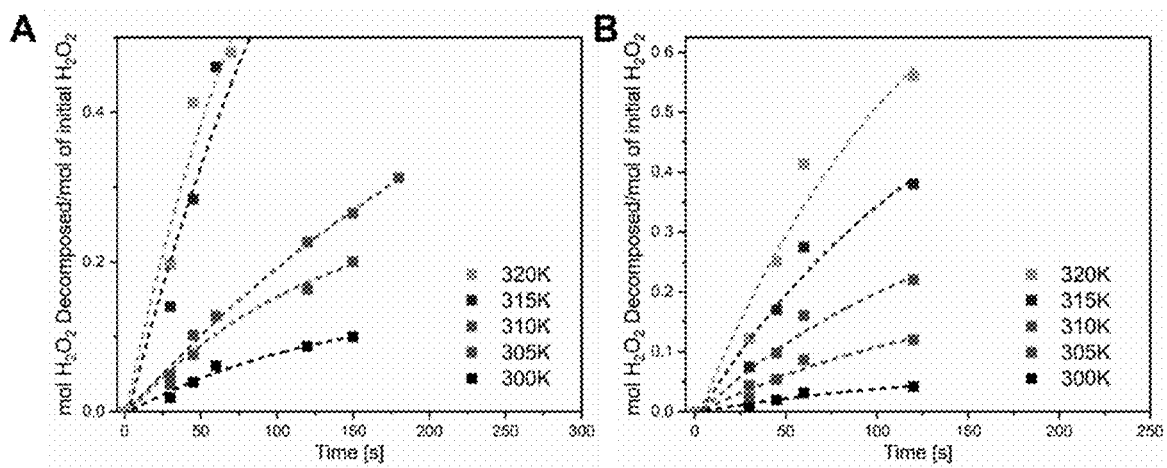

FIG. 16 shows $H_2O_2$ decomposition curve under varying temperature conditions. $H_2O_2$ decomposition curves attained by adding (A) $MnO_2$ nanosheets and (B) lyophilized PLGA/MnO$_2$ particles into H$_2$O$_2$-containing media under different incubation temperatures noted in each figure. The initial H$_2$O$_2$ concentration was kept constant at 0.2 mM. Dash lines are for visual guide.

Figure 17:
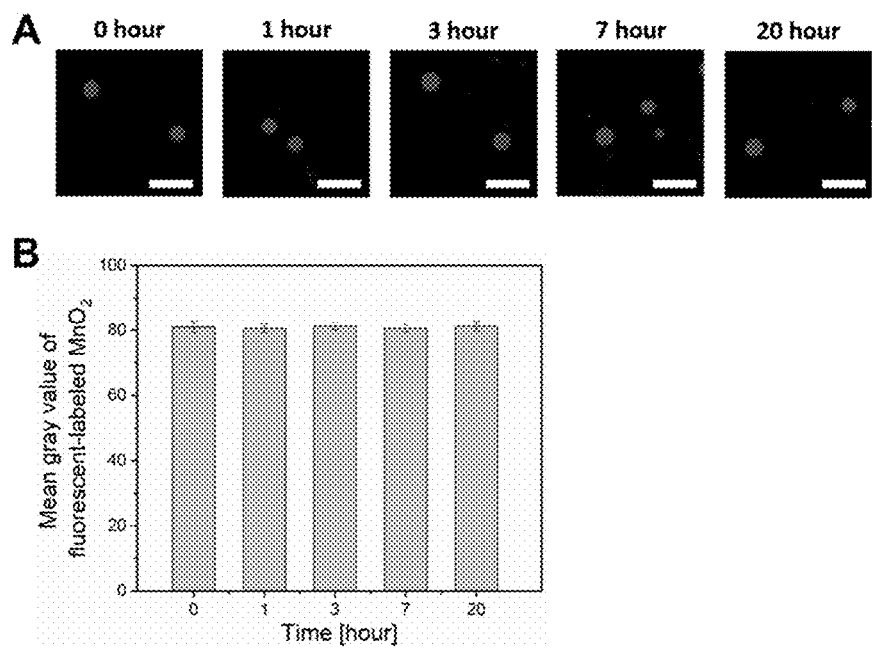

FIG. 17 shows quantitative analysis of fluorescent-labeled MnO$_2$ intensity change over time. (A) Confocal images of PLGA/MnO$_2$ microparticles incubated with H$_2$O$_2$ at different time points. Alginate associating with MnO$_2$ nanosheets were labeled with red-colored rhodamine. Scale bar represents 5 µm. (B) Mean gray value of fluorescence from the PLGA/MnO$_2$ microparticles with H$_2$O$_2$ at different time points. Data points and error bars represent the average and standard deviation of three different samples per condition, respectively.

Figure 18:
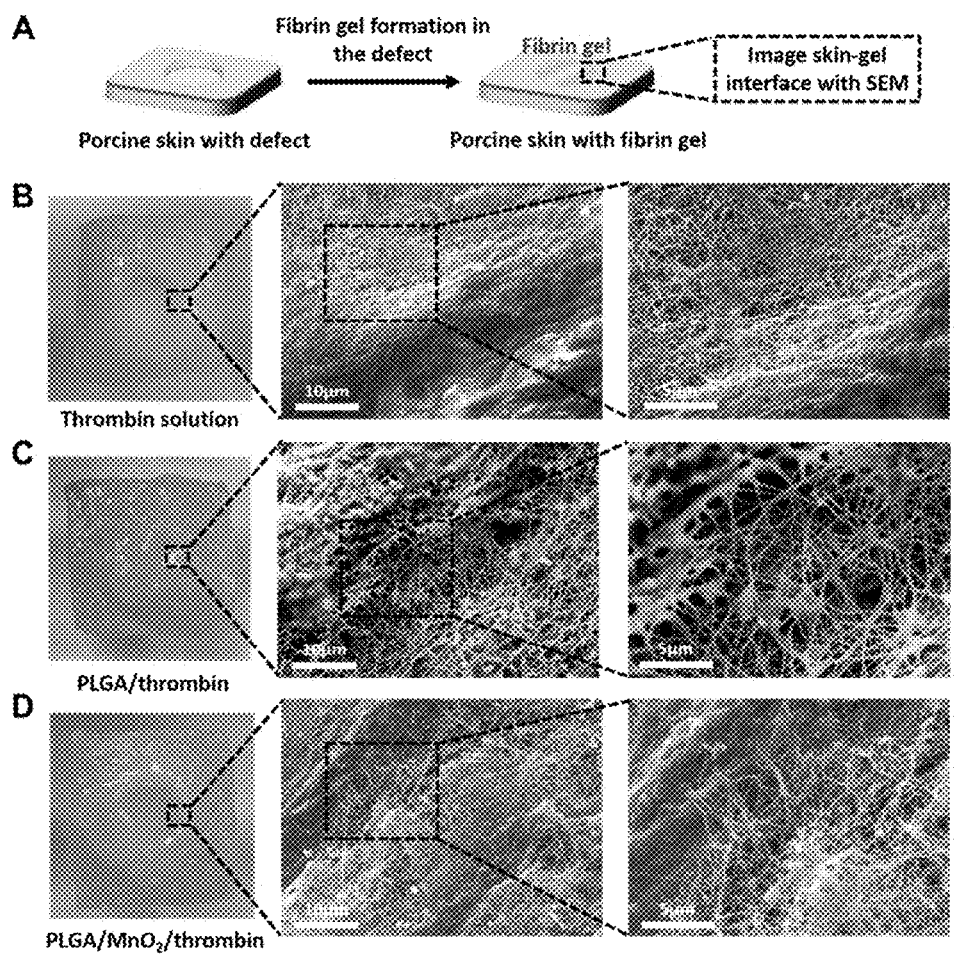

FIG. 18 shows evaluation of the bio-adhesion of fibrin gel. (A) Schematic illustration of the experimental set-up used to evaluate the bio-adhesion of the fibrin gel to a porcine skin explant. The porcine skin explant was punched to simulate wounds where fibrin gels are implanted. The punched wounds were filled with fibrin gels (B-D) SEM images of the interface between skin and fibrin gel. The gel filled a hole created by punching out a center part of the square-shaped porcine skin. (B) Fibrin gel formed by mixing fibrinogen and thrombin solution. (C) Fibrin gel formed by mixing fibrinogen and PLGA/thrombin particles. (D) Fibrin gel formed by mixing fibrinogen and PLGA/MnO$_2$/thrombin particles.

Figure 19:
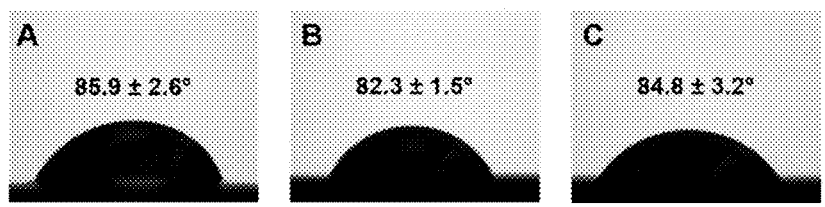

FIG. 19 shows evaluation of surface water contact angle of fibrin gel. Contact angle measurements were taken with a goniometer using water as the test liquid for gel formed by mixing fibrinogen with (A) thrombin, (B) PLGA/thrombin particles, and (C) PLGA/MnO$_2$/thrombin particles.

Figure 20:
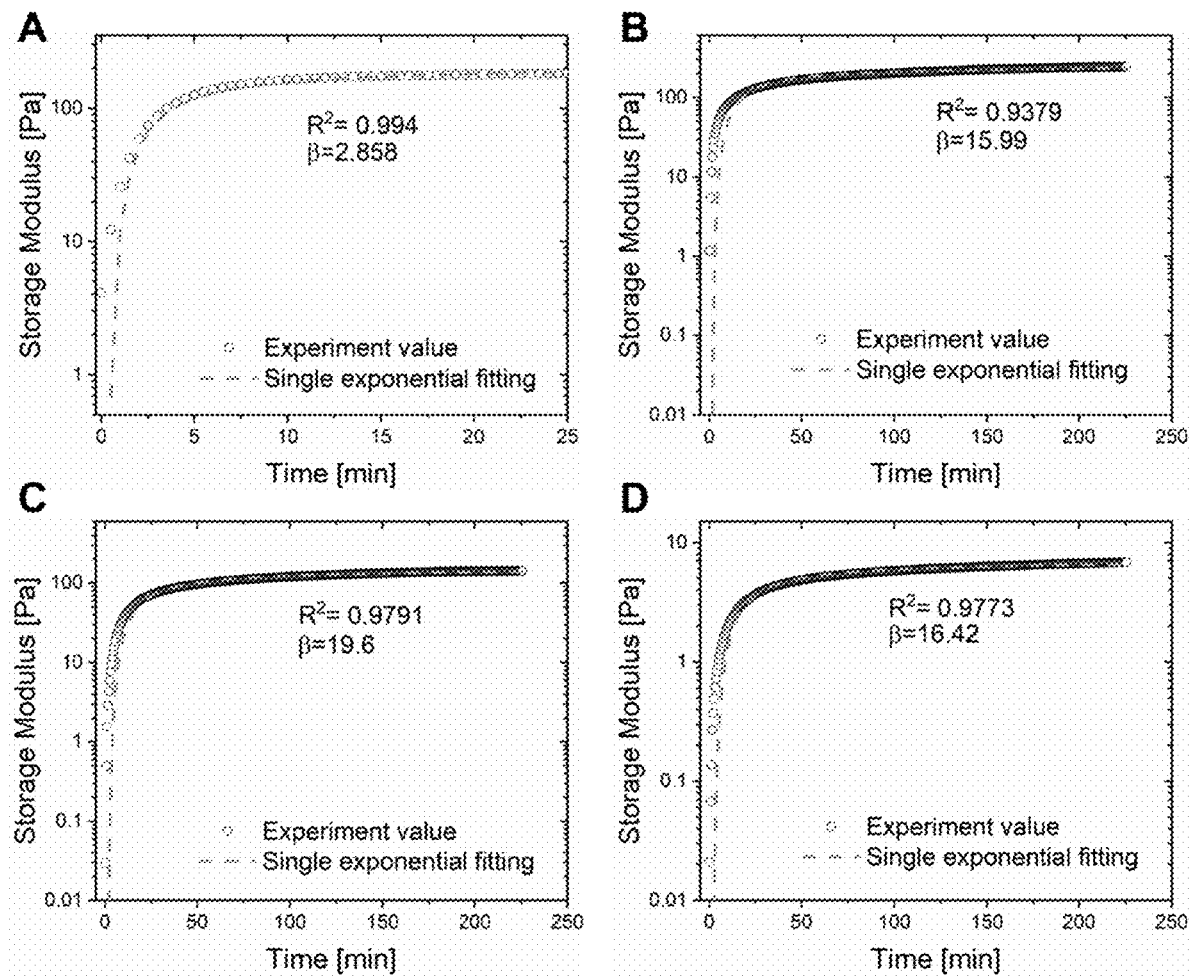

FIG. 20 shows single exponential gelation curve fitting. Single exponential fitting of the gelation curve. (A) Gelation curve attained by mixing thrombin solution with fibrinogen solution. (B) Gelation curve attained by mixing PLGA/MnO$_2$/thrombin particles with a fibrinogen solution. (C) Gelation curve attained by mixing PLGA/thrombin particles with a fibrinogen solution. (D) Gelation curve of the mixture of blank PLGA particles, thrombin solution, and fibrinogen solution.

G'(t)=G'$_{eq}$ exp(-β/t) where G'(t) is the storage modulus, G'$_{eq}$ is the equilibrium storage modulus, β is the characteristic time, and t is time.

Figure 21:
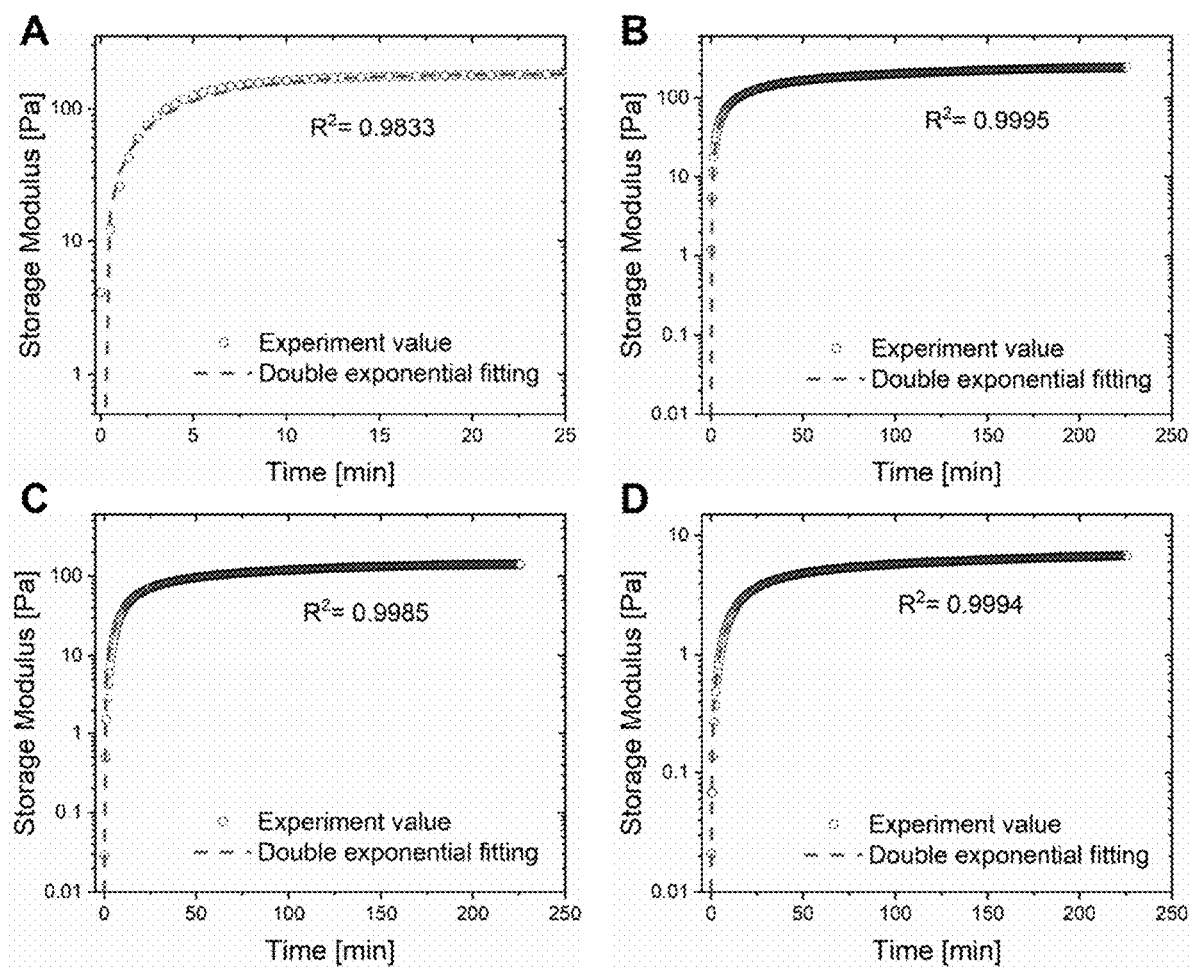

FIG. 21 shows double exponential gelation curve fitting.

$$G'(t) = G'_0 + G'_1\left(1 - \exp\left(-\frac{t}{\tau_1}\right)\right) + G'_2\left(1 - \exp\left(-\frac{t}{\tau_2}\right)\right)$$

where G'(t) is the storage modulus; G'$_0$ is the storage modulus of the pre-gelled solutions; G'$_1$ is the storage modulus contributed by the first branching and crosslinking reaction phase; G'$_2$ is the storage modulus caused by the second lateral growth of fibrin polymers; t is the time; and 1/τ$_1$ and 1/τ$_2$ are the characteristic rates for branching and lateral growth, respectively. Double exponential fitting of the gelation curve. (A) Gelation curve attained by mixing thrombin solution with fibrinogen solution. (B) Gelation curve attained by mixing PLGA/MnO$_2$/thrombin particles with a fibrinogen solution. (C) Gelation curve attained by mixing PLGA/thrombin particles with a fibrinogen solution. (D) Gelation curve of the mixture of blank PLGA particles, thrombin solution, and fibrinogen solution.

Figure 22:
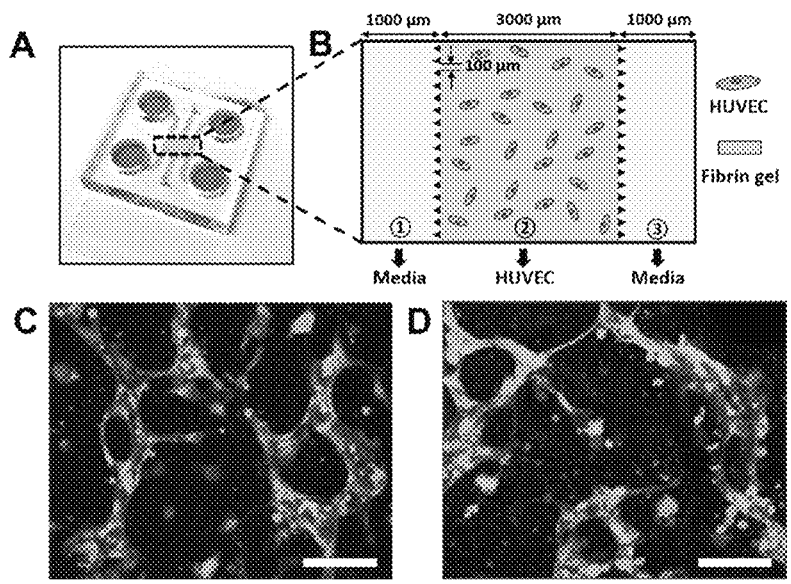

FIG. 22 shows an in vitro angiogenesis assay. (A) Schematic illustration of a microfluidic chip device used for the angiogenesis study in vitro. (B) The central portion features three channels. The fibrin gel encapsulating HUVECs filled the center channel (2); cell culture medium filled channels (1) and (3). Confocal laser scanning microscopic images of tube formation by human umbilical vein endothelial cells seeded in fibrin gel formed by mixing fibrinogen with (C) thrombin solution and (D) PLGA/MnO$_2$/thrombin particles. Cells were immunostained with CD31 (in green). Cell nuclei were stained with DAPI (in blue). Scale bar represents 100 µm.

Figure 23:
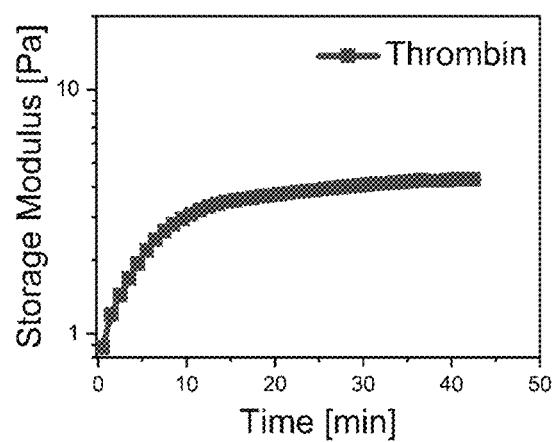

FIG. 23 shows blood clot formation triggered by thrombin. Change in the storage modulus of the blood mixed with a thrombin solution.

DETAILED DESCRIPTION

Catalytic microgelator particles capable of discharging thrombin cargos in response to an external stimulus allow for the decoupling of the dependency between the gelation time and the mechanics of the fibrin gel. Catalytic microgelators also allow users to avoid altering the concentrations of compounds used for fibrin gel assembly that can affect the microstructure and properties of fibrin gels.

Catalytic Microgelator

Catalytic microgelator compositions can comprise a catalyst for the decomposition of hydrogen peroxide (H$_2$O$_2$), and thrombin, wherein the catalyst for the decomposition of hydrogen peroxide (H$_2$O$_2$) and thrombin are encapsulated within a polymer.

Thrombin

Thrombin is an activated enzyme that results from the proteolytic cleavage of prothrombin (factor II). Thrombin acts as a serine protease to convert soluble fibrinogen into insoluble strands of fibrin, as well as catalyzing many other coagulation-related reactions. Thrombin can be obtained by a variety of methods known in the art. For example, thrombin can be made recombinantly and can be derived from plasma. Human thrombin is a 295 amino acid protein composed of two polypeptide chains joined by a disulfide bond. Human and non-human (e.g., bovine) thrombin can be used in the compositions and methods described herein. Thrombin is available from manufacturers such as Johnson and Johnson, Baxter and CSL Behring either as a standalone product, e.g. EVITHROM®, or as a component of a product e.g. EVICEL®, TISEEL®, Beriplast®, and the like. Thrombin or prothrombin can be encapsulated in a polymer and present in a catalytic microgelator particle as described herein. Where prothrombin is used activated Factor X (Xa), and optionally activated Factor V (Va) can be added to a reaction mixture to form thrombin. Therefore, thrombin can be replaced with prothrombin throughout this description, with the subsequent addition of activated Factor X (Xa), and optionally activated Factor V (Va) at, e.g., at or about the time of the addition of the H$_2$O$_2$ or other suitable time.

In an embodiment, thrombin is present in 1 mg of catalytic microgelator particles at about 5, 10, 20, 30, 40, 50, 60, 70, 80, 90, 100, 125, 150, 200 ng or more.

Polymers

A polymer can be, for example, poly(lactic-co-glycolic acid) (PLGA), polyethylene glycol (PEG), polyvinylpyrrolidone (PVP), polypropylene glycol, poly(carboxybetaine), poly(sulfobetaine), poly(carboxybetaine methacrylate) (PCBMA), polylactic acid (PLA), polyglycolic acid (PGA), polybutylene succinate (PBS), polyhydroxyalkanoate (PHA), polycaprolactone acid lactone (PCL), polyhydroxybutyrate (PHB), glycolic amyl acid (PHV), poloxamers, polylactonic acid, hyaluronic acid, cellulose, polyurethane, poly(ethylene vinyl acetate), silicone, polyacrylic acid, polyethylene, polypropylene, polyamide, poly(ester urethane), poly(ether urethane), poly(ester urea), polyether, polyvinyl, parylene, poly(hydroxybutylate), poly(alkyl carbonate), poly(orthoester), polyester, poly(hydroxyvaleric acid), polydioxanone, poly(ethylene terephthalate), poly(malic acid), poly(tartronic acid), polyanhydride, and polyphosphazene, and copolymers thereof (e.g., PHB and PHV copolymer (PHBV), and PLA-polyethylene glycol (PEG) copolymer (PLEG). A polymer can also be, for example, diblock poly(lactic) acid-poly(ethylene)glycol (PLA-PEG) copolymer, diblock poly(lactic acid-co-glycolic acid)-poly(ethylene)glycol (PLGA-PEG) copolymer, and combinations thereof.

In an embodiment a polymer is a biodegradable polymer, (e.g., PLA, PGA, PLGA polymers, derivatives of PLA or PGA, such as PBS, PHA, PCL, PHB, PHV, PHB and PHV copolymer (PHBV), PLEG, etc.). These polymers can degrade in the body by simple hydrolysis of the ester backbone to non-harmful and non-toxic compounds. The in vivo degradation products are either excreted by the kidneys or eliminated as carbon dioxide and water through biochemical pathways.

Catalyst

In an embodiment, a catalyst for the decomposition of hydrogen peroxide is encapsulated in a polymer. In an embodiment $MnO_2$, Pt, CuO, or $ZnO_2$ particles or nanosheets as well as catalase can be used as a catalyst for the decomposition of hydrogen peroxide. $MnO_2$ nanosheets are redox active two dimensional nanomaterials that have thicknesses on the nanometer scale or smaller. The lateral size of $MnO_2$ nanosheets can range from sub-micrometers to micrometers. $MnO_2$ nanosheets have three atomic layers: one Mn layer sandwiched by two O layers. Each Mn coordinates to six O atoms to form edge-sharing $MnO_6$ octahedra. $MnO_2$ nanosheets are negatively charged and repulsive to each other. The d-d transitions of Mn ions in the $MnO_6$ octahedra of $MnO_2$ nanosheets result in a broad absorption spectrum (about 200-600 nm) with a large molar extinction coefficient ($\varepsilon_{max}=9.6\times10^3 M^{-1}$ cm$^{-1}$) at 380 nm. Several methods of making these types of nanosheets are known in the art.

In an embodiment, a catalyst for the decomposition of hydrogen peroxide is present in 1 mg of catalytic microgelator particles at about 1, 2, 3, 4, 5, 6, 6.25, 7, 8, 9, 10, 20, 20, 40, 50, 75 µg or more.

Encapsulation

A catalyst for the decomposition of hydrogen peroxide and thrombin can be encapsulated in a polymer to form a microparticle. Any type of polymer microparticle can be used. A catalyst and thrombin or prothrombin can be entrapped in solid particles where the release of the thrombin is achieved by, for example, degradation of the particles or diffusion out of the particle.

Catalytic microgelator particles can be prepared by microencapsulation, spray drying, precipitation, hot melt microencapsulation, co-extrusion, precision particle fabrication (PPP), or other suitable fabrication techniques. Microencapsulation techniques can use single, double, or multiple emulsion processes optionally in combination with solvent removal step such, as evaporation, extraction, or coacervation step.

The core (e.g., $H_2O_2$ decomposition catalyst and thrombin) and shell (e.g., polymer) can be characterized by a high encapsulation efficiency. As used herein, encapsulation efficiency refers to the relative amount of $H_2O_2$ decomposition catalyst and thrombin in the core, or the amount of polymer in the shell. In some embodiments, the core contains no more than 25%, 20%, 15%, 10%, 7.5%, 5.0%, 2.5%, 1% or 0.5% (w/w) of shell polymer. In some embodiments, the shell contains no more than 25%, 20%, 15%, 10%, 7.5%, 5.0%, 2.5%, 1% or 0.5% (w/w) of $H_2O_2$ decomposition catalyst and thrombin.

The molecular weight of the polymer units that make up the particles can affect the rate of degradation of the particle and subsequent release of the thrombin. For example, particles composed of polymer units having low molecular weights can degrade faster and release the thrombin at an earlier time when compared to particles composed of polymer with high molecular weight polymer units. Particles can comprise polymer units having molecular weights of about 5 kiloDalton (kDa) to about 150 kDa, about 5 kDa to about 125 kDa, about 10 kDa to about 100 kDa, about 15 kDa to about 75 kDa, or about 20 kDa to about 50 kDa, or any individual molecular weight or range encompassed by these example ranges. Specific examples include about 5 kDa, about 10 kDa, about 15 kDa, about 20 kDa, about 25 kDa, about 30 kDa, about 40 kDa, about 50 kDa, about 60 kDa, about 75 kDa, about 100 kDa, about 150 kDa, and ranges in between.

Particles can have a mean particle diameter (MPD) of about 0.1 micrometers (µm) to about 90 µm, about 0.5 µm to about 20 µm, about 0.5 µm to about 50 µm or any range or individual value encompassed by these example ranges. A mean particle diameter of the particles can be about 0.1, 0.5, 0.75, 1.0, 1.25, 1.5, 1.75, 2.0, 2.5, 3.0, 4.0, 5.0, 10, 20, 30, 40, 50 µm or more. A mean particle diameter of the particles can be about 50, 40, 30, 20, 10, 5.0, 4.0, 3.0, 2.5, 2.0, 1.75, 1.5, 1.25, 1.0, 0.75, 0.5, 0.1 0.1 µm or less.

In various embodiments, the catalytic microgelator particles can have $H_2O_2$ decomposition catalyst and thrombin loading of about 0.5 wt. % to about 90 wt. %, about 1 wt. % to about 40 wt. %, about 10 wt. % to about 35 wt. %, about 15 wt. % to about 25 wt. %, or any range or individual value encompassed by these ranges (e.g. about 0.5, 1, 5, 10, 20, 30, 40, 50, 60, 70, 80, 90 wt. % or more). $H_2O_2$ decomposition catalyst and thrombin loading is the weight of $H_2O_2$ decomposition catalyst and thrombin in the final catalytic microgelator particle divided by the weight of particles in the final formulation (units of % w/w; e.g. weight $H_2O_2$ decomposition catalyst and thrombin/weight of shell polymer).

In an embodiment, microgelator particles can be made via a double emulsification ($W_1/O/W_2$) methodology. A water phase ($W_1$) can be prepared by adding thrombin to a suspension of $H_2O_2$ decomposition catalyst (e.g., $MnO_2$ nanosheets). The thrombin can be present at, for example, an about 1:1, 1:2, 1:3, 1:4, or 1:5 ratio to the hydrogen peroxide decomposition catalyst, however, any suitable ratio can be used. An organic phase (O) can be prepared by dissolving a polymer (e.g., PLGA) in a solvent. A solvent can be, for example, any aromatic, halogenated and aliphatic hydrocarbons solvents, such as toluene, xylene, ethers, tetrahydrofuran, chloroform, dichloromethane and heptane. The polymer can be present at an about 20:1, 15:1, 10:1, 10:0.75, 5:1, 2:1, or 1:1 ratio to solvent, but any suitable ratio can be used. Vortex mixing is conducted to form a W1/O emulsion. This primary emulsion (W1/O) can be transferred to an external aqueous phase solution ($W_2$). The external aqueous phase can be, for example, a water soluble polymer. In an embodiment the external aqueous phase is, for example, dodecyl sulfate, sodium dodecylbenzenesulfonate, dioctyl sulfosuccinate sodium, poly(ethylene-alt-maleic anhydride), hexadecyltrimethylammonium bromide, poly(vinyl alcohol), poly(styrene-co-maleic anhydride), polyethylene glycol, polypropylene glycol, polyoxyethylene octyl phenyl ether, polysorbates, sorbitan esters, polyacrylic acid, polyacrylamides, N-(2-Hydroxypropyl) methacrylamide (HPMA), divinyl ether-maleic anhydride (DIVEMA), polyoxazoline, polyphosphates, polyphosphazenes and any combination thereof. The mixture can be vortexed to prepare a secondary emulsion ($W_1/O/W_2$). The mixture can be stirred to evaporate solvent. The resulting particles can be washed and collected by centrifugation.

The ratio of free hydrogen peroxide decomposition catalyst/thrombin to encapsulated hydrogen peroxide decomposition catalyst/thrombin in the compositions described herein can range from about 100:1 to about 1:100, and in certain embodiments, the ratio of free hydrogen peroxide decomposition catalyst/thrombin to encapsulated hydrogen peroxide decomposition catalyst/thrombin can be about 1:1 to about 1:80, about 1:5 to about 1:60, about 1:10 to about 1:50, or any range or individual ratio encompassed by these example ranges. In some embodiments, the composition can include about 0.4 to about 4 mg of free hydrogen peroxide decomposition catalyst/thrombin and about 10 mg to about 30 mg of encapsulated hydrogen peroxide decomposition catalyst/thrombin. Thus, particles can make up about 50 wt. % to about 95 wt. % of the compositions, or about 60 wt. % to about 90 wt. %, about 75 wt. % to about 90 wt. % of the total composition or any range or individual value encompassed by these example ranges.

Catalytic microgelator particles can be lyophilized using any suitable method.

Catalytic microgelators have advantageous properties as compared to the use of thrombin and fibrinogen to product gels or clotting. For catalytic microgelators, the time required to reach a stiffness equal to one half of $G'_{eq}$, denoted $t_{1/2}$, can be about 2, 3, 4, 5, 6, 7, or times of that for a mixture of fibrinogen and thrombin. Additionally, the $G'_{eq}$ can be about 10, 20, 30, 33, 40, 50, 60% or more higher than that for a mixture of fibrinogen and thrombin. Furthermore, the storage modulus of gels or clots produced using catalytic microgelators described herein can (1) continue to increase for 5, 10, 15, 20, 25, 30, 40, 50, 60, 90, 120 minutes or more; and (2) have a Pa of 180, 190, 200, 210, 220, 230, 240, 250, or more. Therefore the use of catalytic microgelators can increase time for gel or clot preparation without a reduced gel rigidity. That is, catalytic microgelator particles can generate gels or clots with a similar microstructure (e.g., similar fibrin fiber diameter, similar number and density of branching points of fibrin) as standard thrombin and fibrinogen solutions with a significant increase in time for gel or clot preparation.

Methods of Making Gels

Figure 1:
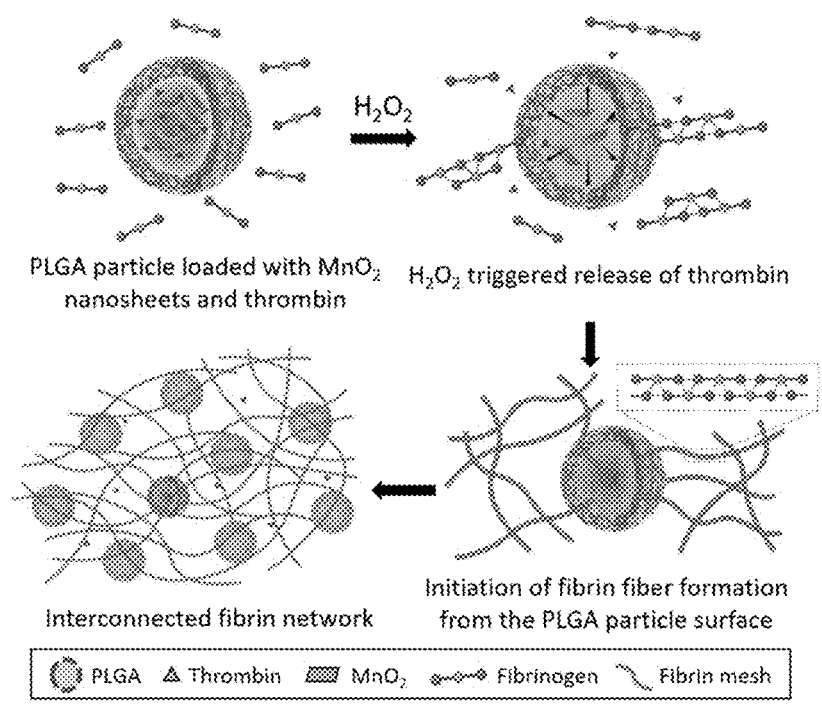
FIG. 1 shows a schematic illustration of the process to form fibrin networks in which fibrin fibers are interconnected with PLGA/$MnO_2$/thrombin particles (i.e., PLGA (poly(D,L-lactide-co-glycolide) particles loaded with catalytic $MnO_2$ nanosheets and thrombin). $H_2O_2$ triggers continuous release of thrombin cargos from PLGA/$MnO_2$/ thrombin particles and, in turn, increase the internal pressure of particles. The released thrombin initiates polymerization of fibrinogen on the PLGA particle surface and promotes the sprouting of fibrin fibers.

Hydrogen peroxide decomposition catalysts, such as manganese oxide nanosheets can catalyze the decomposition of $H_2O_2$ to $H_2O$ and $O_2$ gas. Therefore, catalytic microgelator particles as described herein, when suspended in a media containing $H_2O_2$, can increase the internal pressure by generating $O_2$ gas within their interiors. The increased pressure acts as an outward force to release thrombin cargos. As a consequence, the increase in thrombin concentration around the particle surface increases the number of fibrin fibers that sprout from the particle surface (FIG. 1).

Methods of making a gel are provided herein. In an embodiment a microgelator composition comprising a catalyst for the decomposition of hydrogen peroxide ($H_2O_2$) and thrombin, wherein the catalyst for the decomposition of $H_2O_2$ and thrombin are encapsulated within a polymer is contacted with a fibrinogen solution or powder and $H_2O_2$ to form a mixture. The mixture is allowed to form a gel. Fibrinogen is commercially available from for example Sigma-Aldrich. Fibrinogen can be present in a solution or the mixture at about 0.1, 0.5, 1.0, 1.5, 2.5, 3.0, 3.5, 4.0, 4.5, 5.0, 6.0, 7.0, 8.0, 9.0, 10.0, 11.0, 12.0, 15, 20, 30, 40, 50 mg/ml or more. $H_2O_2$ can be present at about 0.05, 0.1. 0.25, 0.5, 0.6, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0 mM or more. In an embodiment, fibrinogen is present in mass ratio with catalytic microgelator particles of about 1:1, 1:2, 1:3, 1:3.3, 1:4, 1:5, or 1:6.

Gels and Cells

In an embodiment, cells can be added to a mixture prior to gelation so that cells are present within the gel. The cells can be, for example endothelial cells, fibroblast cells, tissue specific cells, or a combination thereof. Endothelial cells can be, for example, adult vein endothelial cells, adult artery endothelial cells, embryonic stem cell-derived endothelial cells, iPS-derived endothelial cells, umbilical vein endothelial cells, umbilical artery endothelial cells, endothelial progenitor cells derived from bone marrow, endothelial progenitor cells derived from cord blood, endothelial progenitor cells derived from peripheral blood, endothelial progenitor cells derived from adipose tissues, or combinations thereof. Umbilical vein endothelial cells can be human umbilical vein endothelial cells (HUVEC). Fibroblast cells can be, for example, human foreskin fibroblasts, human embryonic fibroblasts, mouse embryonic fibroblasts, skin fibroblast cells, vascular fibroblast cells, myofibroblasts, smooth muscle cells, mesenchymal stem cells (MSCs)-derived fibroblast cells, or combinations thereof.

Tissue-specific cells can be, for example, muscle cells, pancreatic beta cells, pancreatic beta-islet cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, bone cells, stem cells, iPS cell derived tissue specific cells, or a combination thereof.

Cells encapsulated in 3D gels can be used as, for example, in tissue engineering, regenerative medicine, angiogenesis studies, in tissue scaffolds, and other compositions and assays.

Methods of Clotting Blood and Blood Products

Methods are provided for clotting blood and blood products (e.g., plasma, serum, platelet rich plasma, etc.). A blood product can naturally contain fibrinogen. Additionally, blood and blood products can optionally have fibrinogen added by the user. $H_2O_2$ can be added to catalytic microgelator particles comprising thrombin and a catalyst for the decomposition of hydrogen peroxide ($H_2O_2$), wherein thrombin and the catalyst for the decomposition of $H_2O_2$ are encapsulated within a polymer. The particles can then be added to blood, plasma, platelet rich plasma (PRP), or any other blood product. Alternatively, the $H_2O_2$ can be added to the blood or blood product and then the catalytic microgelator particles can be added to the blood or blood product.

In an embodiment (a) $H_2O_2$ can be added to catalytic microgelator particles to form a mixture and the mixture can be added to the blood or blood product; or (b) $H_2O_2$ can be added to the blood or blood product to form a mixture and catalytic microgelator particles can be added to the mixture; or (3) $H_2O_2$ and catalytic microgelator particles can be added to the blood or blood product to form a mixture. In an embodiment fibrinogen can optionally be added at any step above, to any component (e.g., to H2O2, to the catalytic microgelator particles, the blood or blood products, or to any of the above mentioned mixtures.

The blood or blood product can then be incubated so that clotting occurs. In an embodiment, fibrinogen can be added to the mixture before adding the mixture to the blood or blood product. Fibrinogen can be present in a solution at about 0.1, 0.5, 1.0, 1.5, 2.5, 3.0, 3.5, 4.0, 4.5, 5.0, 6.0, 7.0, 8.0, 9.0, 10.0, 11.0, 12.0, 15, 20, 30, 40, 50 mg/ml or more. $H_2O_2$ can be present at about 0.05, 0.1. 0.25, 0.5, 0.6, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0 mM or more. In an embodiment, blood or blood product is present in mass ratio with catalytic microgelator particles of about 1:1, 1:2, 1:3, 1:3.3, 1:4, 1:5, or 1:6.

Additional components can be added to a mixture before or after the addition of the microgelator to the fibrinogen solution or blood product, including for example, polymers, emulsifiers, oils, perfumes, proteins, polysaccharides, nucleic acids, microfibrils, antimicrobial agents, adhesive agents, and protease inhibitors.

Methods of Treatment

A method of promoting blood clotting in a subject is provided. $H_2O_2$ can be added to a composition comprising catalyst microgelator particles for the decomposition of $H_2O_2$, and thrombin, wherein thrombin and the catalyst for the decomposition of $H_2O_2$ and are encapsulated within a polymer. The particles can then be administered in an effective amount to the subject. In an embodiment, fibrinogen can be added to the mixture before administering the mixture. Fibrinogen can be present in a solution at about 0.1, 0.5, 1.0, 1.5, 2.5, 3.0, 3.5, 4.0, 4.5, 5.0, 6.0, 7.0, 8.0, 9.0, 10.0, 11.0, 12.0, 15, 20, 30, 40, 50 mg/ml or more. An effective amount is an amount that can cause clotting in the subject. The subject can be a human or any type of mammal (e.g., dog, cat, horse, bovine, sheep, primate, etc.).

Compositions can be administered by any suitable method, for example, parenterally via injection or by the insertion of an indwelling catheter. The compositions can be also be contacted directly with a wound or surgical site.

The subject can have a coagulopathic condition or tissue defect and the method is effective for treating the coagulopathic condition or tissue defect in the subject. The tissue defect can be an external wound, an internal wound, an ulcer, a burn, a natural defect, a surgical incision, or any combination thereof. The tissue defect can be caused by traumatic injury, disease, infection, surgical intervention, natural causes, or any combinations thereof.

The coagulopathic condition can be, for example, vitamin K deficiency, disseminated intravascular coagulation, Von Willebrand disease, hemophilia, aspirin use, thrombocytopenia, early or end-stage liver failure, uremia, congenital afibrinogenemia, Factor V deficiency, Factor X deficiency as seen in amyloid purpura, Glanzmann's thrombasthenia, Bernard-Soulier syndrome, Factor XII deficiency, and C1INH deficiency, hypothermia, and acidosis. The method can further comprise administering a biologically active agent to the subject, such as a second hemostatic agent (e.g., Factor VIIa, thromboxane A2, an anti-inflammatory agent, or an antibiotic agent).

The compositions and methods are more particularly described below and the examples set forth herein are intended as illustrative only, as numerous modifications and variations therein will be apparent to those skilled in the art. As used in the description herein and throughout the claims that follow, the meaning of "a", "an", and "the" includes plural reference unless the context clearly dictates otherwise. The term "about" in association with a numerical value means that the value varies up or down by 5%. For example, for a value of about 100, means 95 to 105 (or any value between 95 and 105).

The terms used in the specification generally have their ordinary meanings in the art, within the context of the compositions and methods described herein, and in the specific context where each term is used. Some terms have been more specifically defined below to provide additional guidance to the practitioner regarding the description of the compositions and methods.

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

Any single term, single element, single phrase, group of terms, group of phrases, or group of elements described herein can be specifically excluded from the claims.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Catalytic microgelator particles designed to discharge thrombin cargos in response to an external stimulus, such as $H_2O_2$, can provide control of the gelation rate over a broad range while strengthening the gel. The examples below demonstrate poly (lactic-co-glycolic acid) (PLGA) particles loaded with thrombin and $MnO_2$ nanosheets that decompose $H_2O_2$ to $O_2$ gas. The resulting catalytic microgelator particles were mixed with fibrinogen solution or blood containing 0.2 mM $H_2O_2$. Due to the increased internal pressure, these particles released a 3-fold larger mass of thrombin than PLGA particles loaded only with thrombin. As a consequence, catalytic microgelators increased the gelation time by one order of magnitude and the elastic modulus by a factor of two compared with the fibrin gel formed by directly mixing fibrinogen and thrombin in solution. These catalytic microgelators also served to clot blood, unlike PLGA particles loaded with thrombin. The resulting blood clot was also more rigid than the blood clot formed by thrombin solution. The catalytic microgelators and methods of use provide a new paradigm in controlling gelation kinetics of pre-gel solution and mechanical properties of the post-gel matrix.

Example 1 Materials and Methods

Materials

Poly(lactic-co-glycolic acid) (PLGA) with an acid end group and molecular weights ranging from 6,000 to 10,000 g/mol (lactic acid: glycolic acid=50:50) was purchased from LACTEL Absorbable Polymers, DURECT (U.S.A). Alginate (MW 250000 g $mol^{-1}$) was obtained from FMC Biopolymer. Cellulose filter was purchased from Millipore Inc. 2-(N-morpholino)ethanesulfonic acid (MES), potassium permanganate ($KMnO_4$), bovine serum albumin (BSA), poly(vinyl alcohol) (PVA, MW=9000-10000), 1-hydroxybenzotriazole hydrate, fluorescein isothiocyanate-dextran (FITC-dextran), neocuproine (>98%), thrombin from human plasma, fibrinogen from human plasma, and fluorescein isothiocyanate-dextran (FITC-dextran) were purchased from Sigma-Aldrich. $H_2O_2$ (30% solution) was purchased from Macron Fine Chemicals. 1-ethyl-3-(dimethylaminopropyl)carbodiimide hydrochloride, Pierce Quantitative Peroxide Assay Kit, dichloromethane (DCM), lissamine rhodamine B ethylenediamine, copper sulfate ($CuSO_4$, >98.6%), and fibrinogen from human plasma Alexa Fluor™ 488 conjugate were purchased from Thermo Scientific. XTT cell proliferation assay kit was purchased from Trevigen. Human thrombin ELISA kit was purchased from Innovative Research. Phosphate buffer saline was purchased from Corning. Ethanol (100%) was purchased from Decon Laboratories.

Synthesis of Fluorescently Labeled Alginate and Water-Dispersible $MnO_2$ Nanosheets Alginate (0.5 mmol uronic acids) dissolved in MES buffer was labeled with lissamine rhodamine B ethylenediamine using aqueous carbodiimide chemistry. 1-Hydroxybenzotriazole hydrate (0.08 mmol), lissamine rhodamine B ethylenediamine (0.0008 mmol), and 1-ethyl-3-(dimethylaminopropyl)carbodiimide hydrochloride (0.16 mmol) were added sequentially to the alginate solution. The reaction mixture was stirred at room temperature and protected from light for 4 hours. Then, the fluorescently labeled alginate was purified by dialysis against DI water over 2 days and finally lyophilized. Filtered alginate was prepared by dissolving alginate in 0.2 M MES buffer (pH 6) at a concentration of 1.0% (w/v). Then, the alginate solution was filtered with 0.22 μm cellulose filter and freeze-dried. The water-dispersible $MnO_2$ nanosheets were prepared by mixing 2.0% (w/v) alginate solution prepared with 0.2 M MES buffer with 50 mM $KMnO_4$ at 1:1 ratio. The mixture was sonicated for 30 min.

Assembly of PLGA Particles Loaded with Human Thrombin and $MnO_2$ Nanosheets (PLGA/$MnO_2$/Thrombin Particles)

PLGA/$MnO_2$/thrombin particles were prepared via double emulsification ($W_1$/O/$W_2$). Water phase ($W_1$) was prepared by adding 50 μL thrombin (100 NIHU/mL) to a 150 μL suspension of $MnO_2$ nanosheets. The organic phase was prepared by dissolving 10 mg of PLGA in 0.75 mL of dichloromethane (DCM). Vortex mixing was conducted to form the W/O emulsion. This primary emulsion was then transferred to 6 ml of 1% (w/v) PVA solution (W2). Then, the mixture was vortexed again to prepare the secondary emulsion ($W_1$/O/$W_2$). The mixture was continuously stirred for 4 hr to evaporate DCM. The resulting particles were washed three times and collected by centrifugation at 2,000 rpm for 10 min. In parallel, PLGA particles loading thrombin were assembled by following the same procedure in the absence of $MnO_2$ nanosheets.

Characterization of PLGA/$MnO_2$/Thrombin Particles

The optical and confocal microscopic images of PLGA particles were obtained by the optical microscope (Leica DMIL) and confocal microscope (LSM 700, Zeiss), respectively. For scanning electron microscopy (SEM) imaging of particles, PLGA particle suspensions were frozen at −20° C. and then lyophilized. The SEM images of PLGA microparticles were obtained with the HITACHI S-4700 microscope operating at 5.0 kV. The elemental analysis of manganese within PLGA particles was conducted with the inductively coupled plasma atomic emission spectroscopy (ICP/AES). The size distribution of particles was obtained by image analysis using the ImageJ software (NIH Image).

Molecular interactions between the PLGA, $MnO_2$ nanosheets, and thrombin were investigated using vibrational spectroscopy. Samples (~3 mg) were pressed onto the diamond internal reflection element (IRE) of an attenuated total reflectance infrared spectrometer (ATR-IR; Bruker, Alpha). Spectra were recorded at ambient conditions (64 scans, 2 $cm^{-1}$ resolution) with a clean diamond IRE as the background.

Characterization of Reactivity of PLGA/$MnO_2$/Thrombin Particles

Initial $H_2O_2$ decomposition rates were measured using a batch reactor with a volume of 20 $cm^3$. $H_2O_2$ was added to PBS and heated to the desired temperature (300-320 K) while stirring the mixture at 800 rpm. $H_2O_2$ decomposition was initiated by adding PLGA/$MnO_2$ particles or $MnO_2$ nanosheets. Small aliquots (~0.5 mL) were extracted through a 0.22 μm syringe filter as a function of time. These aliquots were immediately titrated with an aqueous solution of $CuSO_4$ (8.3 mM), neocuproine (12 mM), and ethanol (25% v/v). The concentration of $H_2O_2$ in each aliquot was quantified with the absorbance at 454 nm using a visible-light spectrophotometer (Spectronic, 20 Genesys). The absorbance was back-calculated to the concentration of $H_2O_2$ using a standard curve made with solutions of known $H_2O_2$ concentration.

The long-term $H_2O_2$ decomposition over 7 hours was analyzed by adding 10 mg of PLGA particles into PBS with 0.2 mM $H_2O_2$ and incubating them at 37° C. The mixture was shaken at 100 rpm. At different time points (1, 3, and 7 hours), the supernatant was collected by centrifuging PLGA particles. The $H_2O_2$ concentration was quantified using the Pierce Quantitative Peroxide Assay Kit.

Characterization of Thrombin Release from Particles

The mass of thrombin released from PLGA/$MnO_2$/thrombin or PLGA/thrombin particles was measured by suspending 10 mg of particles in 1 mL of PBS mixed with 0.2 mM $H_2O_2$ and incubating them at 37° C. The mixture was shaken at 100 rpm. At different time points (1, 3, 7, and 20 hours), the supernatant was collected by centrifuging PLGA particles. The thrombin concentration was determined using a thrombin ELISA kit.

Microstructure and Bioadhesion Analysis of Fibrin Gel

The microstructure of the fibrin gel was analyzed by imaging the fibrous structure using a scanning electron microscope (HITACHI, S-4700). Fibrin gels were prepared by mixing 500 µL fibrinogen (2.5 mg/ml)/$H_2O_2$ (0.2 mM) solution with 5 mg PLGA/$MnO_2$/thrombin or PLGA/thrombin particles. Control fibrin gels were prepared by mixing thrombin and fibrinogen solutions. The thrombin concentration was adjusted to be same across conditions. After gelation overnight, the resulting fibrin gels were washed three times (5 min per wash) in DI water. Then the fibrin gels were dehydrated with an increasing percentage of ethanol. In particular, the gel samples were immersed in 30, 50, and 70% of ethanol sequentially for 1 hr. The fibrin gels were transferred to 100% ethanol and dehydrated overnight. After dehydration, the fibrin gels were dried with $CO_2$ using a critical point dryer (Tousimis). SEM images of the gels coated with Pt were taken using the HITACHI S-4700 microscope operating at 5.0 kV.

The bioadhesion of the fibrin gel was analyzed by visualizing the gel-skin interface using a scanning electron microscope (FEI, Quanta FEG 450 ESEM). Fibrin gels were prepared by mixing fibrinogen with thrombin solution, PLGA/$MnO_2$/thrombin particles, or PLGA/thrombin particles using the concentration mentioned in the microstructure study. The gel was placed in the wound-mimicking hole punched on the porcine skin explant. After gelation for 1 hr, the resulting fibrin gel was dehydrated with an increasing percentage of ethanol. In particular, the gel samples were immersed in 30, 50, and 70% of ethanol sequentially for 1 hr. The fibrin gels were transferred to 100% ethanol and dehydrated overnight. After dehydration, the fibrin gels were dried with $CO_2$ using a critical point dryer (Tousimis). SEM images of the gel-skin interface coated with Pt were taken using the FEI Quanta FEG 450 ESEM operating at 10.0 kV.

The water contact angle was measured using a contact angle goniometer (Rame-Hart). After leveling the instrument, 5 µL of deionized water droplet was placed on gel surface. The images of the droplets on the various surfaces were taken and the instrument software was used to quantify the contact angle. Fresh samples were used for each replicate measurement.

In Situ Confocal Imaging of Fibrin Gel Formation

The fibrous networks evolved during the gelation were imaged using a confocal microscope (LSM 700, Zeiss). The pre-gel solution consisting of fluorescently labeled fibrinogen (2.5 mg/mL) and $H_2O_2$ (0.2 mM) was mixed with rhodamine-labeled PLGA or PLGA/$MnO_2$ particles. In this study, fibrinogen was labeled with Alexa-488, while alginate coupled with $MnO_2$ nanosheets was labeled with rhodamine. PLGA particles free of $MnO_2$ nanosheets were labeled by loading rhodamine-labeled alginate via double-emulsification. The pre-gelled mixture was immediately transferred to a microscope slide with a 0.26 mm spacer and capped with a cover slide. The fibrin gel formation was monitored every 10 min for 1 hour by imaging green-colored fibrin fibers that developed over time.

Analysis of the Biomolecular Diffusion in the Fibrin Gel

The diffusion coefficient of dextran probes within the fibrin gel was measured using the FRAP (fluorescence recovery after photobleaching) assay. The pre-gelled mixture that contains fibrinogen (2.5 mg/mL), $H_2O_2$ (0.2 mM) and PLGA particles were mixed with 2 mg/mL fluorescein-conjugated dextran. Then, the solution was transferred to the microscope slide with a 0.26 mm spacer and capped with a cover slide. After gelation, the FRAP assay was performed using a multi-photon confocal microscope equipped with a FRAP module (LSM 710, Zeiss). A circle spot with a diameter of 0.2 mm was photobleached using a 488 nm argon laser. After photobleaching, the fluorescent image and intensity were recorded every 1 s for 150 sec. The fluorescence intensity (F) over time (t) was plotted and fitted using the equation (5)

$$F=A_1+A_2 \exp(-[2T/t]) \tag{5}$$

Where $A_1$ is the initial fluorescence intensity, $A_2$ is the modified Bessel function, and T is the recovery time constant. The diffusion coefficient (D) was then calculated using the equation (6)

$$D=R^2/4T \tag{6}$$

where R is the radius of the photobleached spot.

Rheological Characterization of Gelation Kinetics and Mechanical Property of Fibrin Gel The gelation process was monitored with small amplitude oscillatory shear rheology using an MCR702 rheometer (Anton Parr) with a parallel plate configuration (25 mm). Reaction mixtures comprised of fibrinogen (12 mg/mL) and $H_2O_2$ (0.2 mM) were mixed in a centrifuge tube with a total volume of 0.5 mL. After the addition of PLGA/$MnO_2$/thrombin particles (20 mg) or PLGA/thrombin particles (20 mg), the reaction components were thoroughly mixed with a pipette tip. Then, the mixture was quickly transferred from the tube to the rheometer bottom plate. Measurements of the storage and loss moduli were taken at 0.1 Hz under an imposed strain amplitude of 1%. Data points were recorded every 30 seconds, and the gelation process was monitored until the moduli reached a plateau. The temperature was maintained at 37° C. using a Peltier heat exchanger. The control fibrin gel was prepared by mixing fibrinogen and thrombin solution. The thrombin concentration was kept the same as the amount of thrombin released from the PLGA/$MnO_2$/thrombin particles over 7 hours.

In Vitro Angiogenesis Assay

HUVECs were suspended in the fibrinogen solution (2.5 mg/mL) containing $H_2O_2$ (0.2 mM) at a concentration of $4\times10^6$ cells/mL. PLGA/$MnO_2$/thrombin fibrin gel was prepared by mixing cell suspension with PLGA/$MnO_2$/thrombin particles. Then, the pre-gel solution was immediately introduced to the center HUVEC channel. The mass ratio between fibrinogen and particles was kept constant at 1:4. The control fibrin gel was prepared by mixing cell suspension with thrombin. The thrombin concentration was kept the same as the amount of thrombin released from the PLGA/$MnO_2$/thrombin particles over 7 hours. The cell suspension-gel constructs were allowed to gel for 5 min at room temperature. To fill the outer channel, the inlet reservoirs of the cell culture media channels were loaded with EGM-2 supplemented with 3 ng/mL of VEGF. The vacuum was then applied at the outlet reservoirs. Following the loading of all four reservoirs, the microfluidic platforms were incubated at 37° C. and 5% $002$. The cell culture medium was removed and refilled with fresh EGM-2 culture medium every 24 h.

After 3 days, cells were washed once with PBS and fixed in methanol-acetone solution (1:1 ratio) for 20 min at −20° C. After blocking with 3% BSA in PBS for 1 h, samples were incubated overnight at 4° C. with CD31 primary antibodies directly conjugated with a fluorescent marker (1:20). The cell nuclei were stained with DAPI (1:50) for 20 min at room temperature. The chips were washed three times and stored in PBS before imaging.

Rheological Characterization and Microstructure Analysis of Blood Clots

PLGA/$MnO_2$/thrombin particles (40 mg) or PLGA/thrombin particles (40 mg) were lyophilized and mixed with $H_2O_2$ (0.2 mM) before adding them into 1 mL of porcine blood. Blood was mixed with 3.2% citrate to prevent coagulation. The process of blood clotting was monitored by conducting SAOS rheology. After mixing of blood with particles of interests, 0.5 mL of the mixture was transferred to the bottom plate of the MCR 702 rheometer. For the control group, the pre-gel solution was prepared by mixing 1 mL of porcine blood with an equal amount of thrombin that was released by PLGA/$MnO_2$/thrombin particles over 7 hours.

To visualize the resulting blood clots, the sample mixtures mentioned above were pipetted into a centrifuge tube and flipped every 10 minutes. Scanning electron microscope (Hitachi, S-4800) was used to visualize the microstructure of the fully clotted blood clots formed by PLGA/$MnO_2$/thrombin particles. The sample was prepared in a cylindrical polydimethylsiloxane (PDMS) mold. After one hour, each sample was rinsed with PBS and fixed in the Karnovsky fixative overnight at 4° C. Then, the fibrin clots were rinsed with PBS and fixed with 1% osmium tetraoxide for an hour. The clots were rinsed in distilled water and dehydrated by increasing concentration of ethanol gradually. The resulting clots were immersed in 30, 50, and 70% of ethanol sequentially for 1 hr per ethanol concentration. Then, the clot was transferred to 100% ethanol and dehydrated overnight. The dehydrated gel was dried with $CO_2$ using a critical point dryer (Tousimis). SEM images of the clots coated with Pt were taken with HITACHI S-4800 microscope operating at 2.0 kV.

In Vivo Hemostatic Performance Analysis

To examine the in vivo hemostatic ability of the PLGA/$MnO_2$/thrombin and PLGA/thrombin particles, a rabbit (healthy male New Zealand white rabbit, 3.2-3.5 kg) hemorrhaging liver model was used (n=3 per group). Animal care and experimental procedures were conducted in accordance with the guidelines approved by the Institutional Animal Care and Use Committee (IACUC) at Yonsei University Health System, Seoul, Korea (IACUC approval No. 2017-0351). Briefly, 5 mg/kg of xylazine and 15 mg/kg of Zoletil® was intramuscularly injected every 15 min as premedication. After intubation with a 3.0 or 3.5 mm endotracheal tube, 2.0% isoflurane was used to maintain inhalation anesthesia. All the animals received crystalloid solution (10 mL/kg/h) throughout the surgical procedure. After abdominal incision, the bleeding was induced using a biopsy punch (Integra Miltex) to create a 3 mm (diameter) defect. As a negative control, time to hemostasis was measured without any treatment. PLGA/$MnO_2$/thrombin particles or PLGA/thrombin particles were lyophilized and mixed with $H_2O_2$ (0.2 mM) before applying on the bleeding site. 0.25 ml of particle solution at a concentration of 40 mg/ml were treated in each defect site. The time to hemostasis was measured with and without treatment of the particle solution.

Analysis of the Toxicity of Thrombin Carriers

Mouse endothelial cell line, C166 (ATCC CRL2581), was maintained in Dulbecco's Modified Eagle Medium (DMEM) growth media supplemented with 10% FBS, 1 mM sodium pyruvate, 100 U/mL penicillin and 100 mg/mL streptomycin, and cultured at 37° C., under an atmosphere of 5% $CO_2$ and 95% humidified air. C166 cells were seeded onto 96-well plates at a density of 5000 cells per well one day before treatment. For a certain experiment, the cell culture media was mixed with $H_2O_2$ to make the $H_2O_2$ concentration being 0.2 mM. Different concentrations of PLGA or PLGA/$MnO_2$ particles were prepared by serial dilutions in the cell culture media. The cells were then incubated with particles. 0.1 mL of PLGA or PLGA/$MnO_2$ particle suspension was added to each well. After 24 hr, 0.1 mL of growth media and 0.05 mL of XTT cell proliferation assay kit working solution were then added to each well. The cells were incubated for 3 h at 37° C. The absorbance values of the solution at a wavelength of 490 and 630 nm were measured by using the microplate spectrophotometer (TECAN, Infinite 200 Pro). The relative metabolic activity of cells was quantified as $[(A_{490}-A_{630})$ of each group/$(A_{490}-A_{630})$ of control group] where $A_{490}$ and $A_{630}$ represent absorbance at 490 nm and 630 nm respectively. The control group represents the group in which only media was added to each well.

Statistical Analysis

Three samples were analyzed per condition, and the data were presented as mean±standard deviation unless otherwise specified. To determine significance, comparisons between groups were performed by one-way ANOVA followed by Tukey's post hoc analyses. Data were considered significant for p values less than 0.05.

Example 2 Preparation and Characterization of PLGA/$MnO_2$ Particles Encapsulating Thrombin (PLGA/$MnO_2$/Thrombin Particles)

Figure 11:
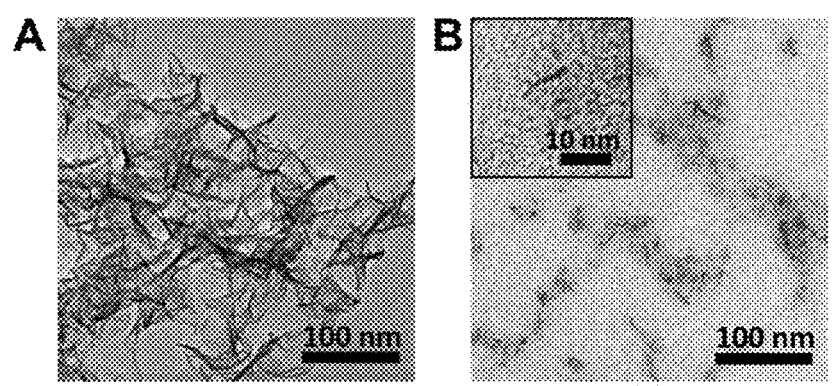
FIG. 11 shows TEM images of (A) alginate-free $MnO_2$ nanosheets and (B) $MnO_2$ nanosheets complexed with alginate, denoted as $MnO_2$ nanosheets.
Figure 12:
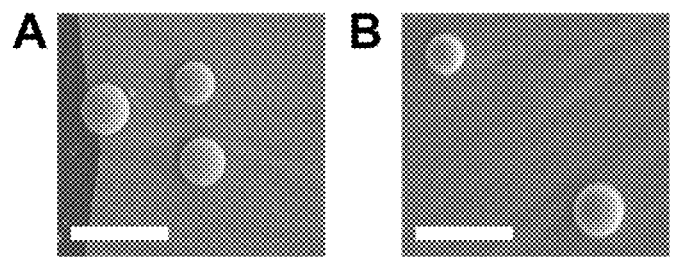
FIG. 12 shows SEM images of (A) PLGA particles and (B) PLGA/$MnO_2$ particles. Scale bar represents 5 µm.
Figure 13:
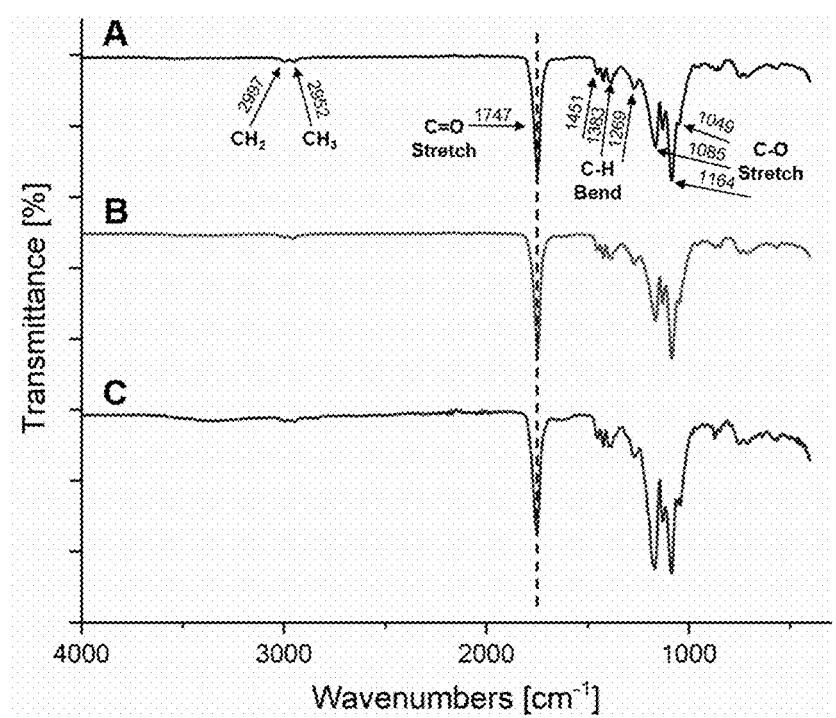
FIG. 13 shows FTIR spectra of (A) Blank PLGA (B) PLGA/$MnO_2$ (C) PLGA/$MnO_2$/thrombin particles.

PLGA/$MnO_2$ particles that release thrombin in response to $H_2O_2$ were assembled by encapsulating $MnO_2$ nanosheets and thrombin molecules through the double emulsification. Mixing $KMnO_4$ with alginate dissolved in 2-(N-morpholino)ethanesulfonic acid (MES) buffer in 1:1 ratio resulted in the $MnO_2$ nanosheets dispersed in water via reduction of $KMnO_4$ and simultaneous complexation with alginate (FIG. 11). The resulting spherical PLGA/$MnO_2$ particles possess a mean diameter of 1.6±0.6 µm, as confirmed with optical microscope images (FIGS. 2B and 2C). The incorporation of $MnO_2$ nanosheets in the PLGA particles did not result in a significant change in the diameter of particles and the molecular interaction between the particles (FIG. 12, 13). The presence of $MnO_2$ nanosheets in the PLGA particle was confirmed by complexing the nanosheets with the rhodamine-conjugated alginate (FIG. 2D). The spherical morphology of the PLGA particle was also confirmed by SEM (FIG. 2E).

The mass of $MnO_2$ nanosheets loaded in 1 mg of particles could be controlled from 0.0625 to 6.25 µg by altering the initial concentration of $MnO_2$ nanosheets added to the aqueous media during the double emulsification. The loading mass of thrombin was minimally affected by the loading mass $MnO_2$ nanosheets in the particles. According to the thrombin ELISA kit, 1 mg of PLGA and PLGA/$MnO_2$ particles carried 72±1.6 ng of thrombin. The small loading error range influenced the drug release profile insignificantly. The potential toxicity of the PLGA and PLGA/$MnO_2$ particles was evaluated by measuring the metabolic activity of endothelial cells incubated with these particles for 24 hrs. Up to the particle concentration of 10 mg/mL, more than 70% of cells remained metabolically active (FIG. 2F).

Example 3. Kinetic Study of $H_2O_2$ Decomposition by PLGA/$MnO_2$ Particles

Figure 3:
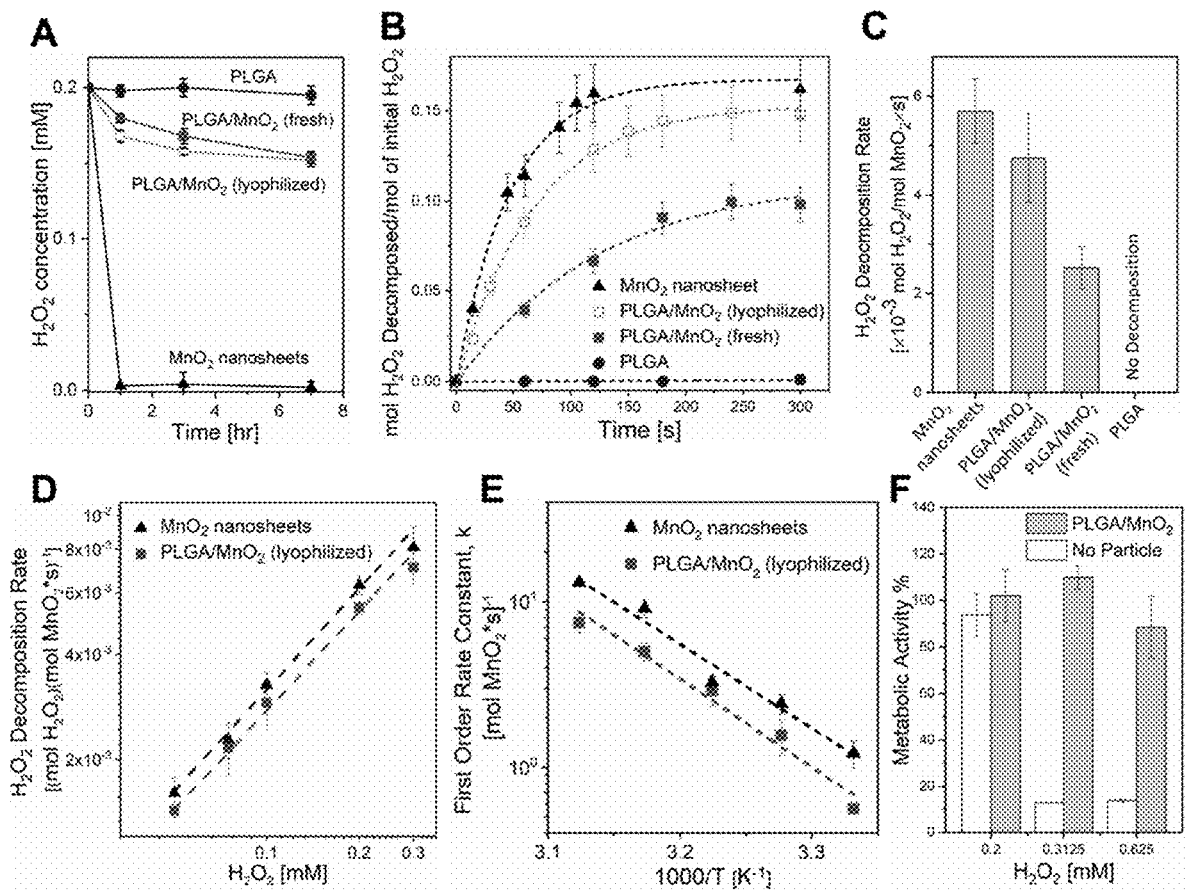
FIG. 3 shows kinetic and thermodynamic analysis of the $H_2O_2$ decomposition activated by PLGA/$MnO_2$ particles, PLGA particles, and free $MnO_2$ nanosheets. (A) Measurement of the $H_2O_2$ concentration change over time. Particle concentration in the $H_2O_2$ solution was kept constant at 5 mg/ml. (B) The mole of $H_2O_2$ decomposed per mole of initial $H_2O_2$ during the first 5 min. Particle concentration in the $H_2O_2$ solution was kept constant at 1 mg/ml. Dashed lines are for visual guide. (C) Initial $H_2O_2$ decomposition rate quantified by fitting curves in (B). (D) The dependency of the decomposition rate on the $H_2O_2$ concentration for free $MnO_2$ nanosheets (▲) and lyophilized PLGA/$MnO_2$ particles (▓). (E) Dependence of the decomposition rate on temperature for free $MnO_2$ nanosheets (▲) and lyophilized PLGA/$MnO_2$ particles (▓). (F) Metabolic activity of C166 endothelial cells after incubation with PLGA/$MnO_2$ particles in 0.2-0.625 mM $H_2O_2$ solution. In (A)-(F), each data point and error bar represent the average and standard deviation of three different samples per condition, respectively. In this study, the mass of $MnO_2$ in the 1 mg of PLGA/$MnO_2$ particles was kept constant at 6.25 µg.

The extent to which PLGA/$MnO_2$ particles take up and decompose $H_2O_2$ was examined by measuring peroxide-induced oxidation of ferrous to ferric ions. Both fresh and lyophilized PLGA/MnO$_2$ particles decreased H$_2$O$_2$ concentration from 0.2 to 0.15 mM continuously over 7 hours (FIG. 3A). In contrast, the direct addition of MnO$_2$ nanosheets to the H$_2$O$_2$ solution resulted in rapid decomposition. The H$_2$O$_2$ concentration decreased from 0.2 Mm to almost 0 mM within an hour. In addition, blank PLGA microparticles did not decompose H$_2$O$_2$.

Figure 14:
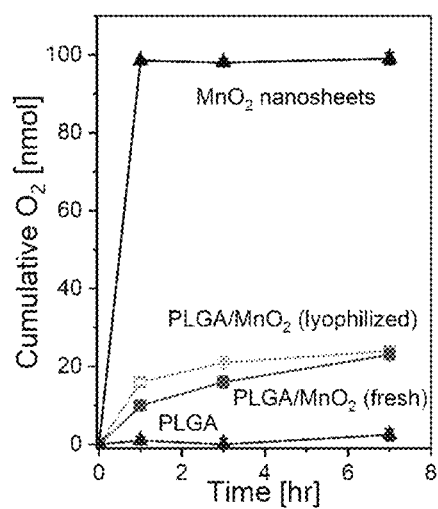
FIG. 14 shows cumulative $O_2$ generated through the $H_2O_2$ decomposition. The cumulative $O_2$ was quantified by calculating the amount of $H_2O_2$ that was decomposed. Data points and error bars represent the average and standard deviation of three different samples per condition, respectively.

The amount of O$_2$ generated was calculated within the particle by using the stoichiometric relationship between decomposed H$_2$O$_2$ and generated O$_2$ (FIG. 14). According to the calculation, both fresh and lyophilized PLGA/MnO$_2$ particles produced O$_2$ gas continuously up to 7 hours. The lyophilized PLGA/MnO$_2$ particles generated O$_2$ gas more actively than fresh ones, likely due to the more rapid diffusion of H$_2$O$_2$ into the particle.

We further examined the kinetics of H$_2$O$_2$ decomposition by monitoring visible absorbance at 454 nm, after titration with a Cu$^{II}$ and neocuproine (FIG. 3B). The initial H$_2$O$_2$ decomposition rate was quantified with a slope of the linear portion of each curve shown in FIG. 3B. The H$_2$O$_2$ decomposition rate by lyophilized PLGA/MnO$_2$ particles was twice as high as that observed by fresh PLGA/MnO$_2$ particles (FIG. 3C). This result also suggests that H$_2$O$_2$ diffuses into lyophilized PLGA/MnO$_2$ particles more rapidly than fresh particles due to pore formation in the particle shell after lyophilization. The decomposition rate by blank PLGA particles was zero.

In addition, the degree that H$_2$O$_2$ decomposition rate depends on the H$_2$O$_2$ concentration during reactions on MnO$_2$ nanosheets was evaluated (FIG. 3D and FIG. 15). The decomposition activity of lyophilized PLGA/MnO$_2$ particles was compared with that of free MnO$_2$ nanosheets. The decomposition rate exhibited a nearly linear dependence on H$_2$O$_2$ concentration for both free MnO$_2$ nanosheets (rate ~[H$_2$O$_2$]$^{0.9\pm0.04}$) and lyophilized PLGA/MnO$_2$ particles (rate ~[H$_2$O$_2$]$^{0.9\pm0.05}$).

The activation energy for H$_2$O$_2$ decomposition (Ea) was calculated by fitting the curve of the decomposition rate constant (k; calculated by assuming a pseudo-first-order rate expression on H$_2$O$_2$ concentration) versus inverse temperature to the Arrhenius equation.

$$k = ve^{\left(\frac{-E_a}{RT}\right)} \quad (1)$$

Where v is the pre-exponential factor, R is the ideal gas constant, and T is the absolute temperature (FIG. 3E and FIG. 16). The activation energy with free MnO$_2$ nanosheets (44±4 kJ/mol) is comparable to Ea attained with lyophilized PLGA/MnO$_2$ particles (49±5 kJ/mol). The similarity of the H$_2$O$_2$ decomposition rates, power-law dependencies, and activation energies suggest that the integration of MnO$_2$ nanosheets into PLGA particles does not significantly affect the rate or the mechanism for H$_2$O$_2$ decomposition on these materials.

The lyophilized PLGA/MnO$_2$ particles were able to protect cells from H$_2$O$_2$ (FIG. 3F). Endothelial cells were exposed to the H$_2$O$_2$ or the mixture of H$_2$O$_2$ and PLGA/MnO$_2$ particles for 24 hours and the metabolic activity of cells was examined. 90% of cells lost metabolic activity in the media containing 0.3 and 0.6 mM H$_2$O$_2$. In contrast, approximately 90% of cells incubated with PLGA/MnO$_2$ particles remained metabolically active up to 0.6 mM H$_2$O$_2$ solutions. This protective effect is due to the uptake and decomposition of H$_2$O$_2$ by the MnO$_2$ within the PLGA/MnO$_2$ particles.

Example 4. Analysis of Thrombin Release from Particles

Figure 4:
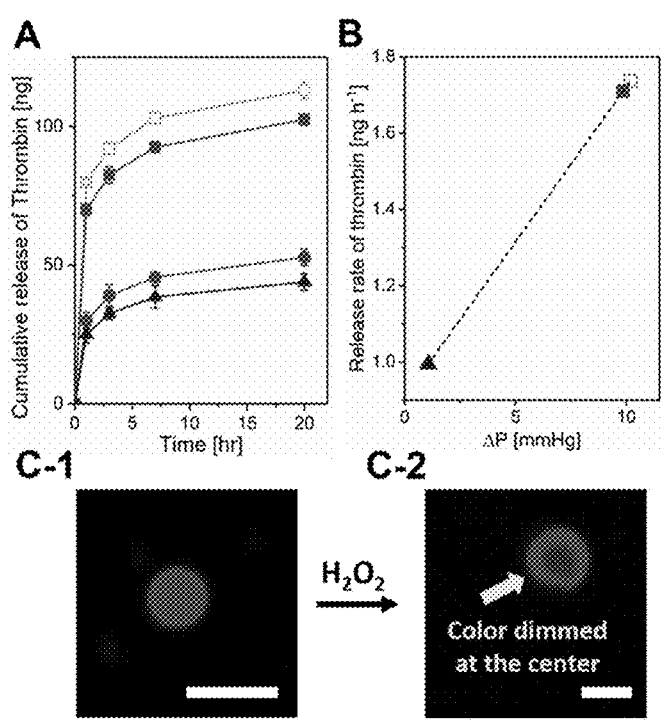
FIG. 4 shows analysis of the $H_2O_2$-triggered thrombin release profile and underlying mechanism (A) Cumulative release profile of thrombin from the PLGA/$MnO_2$/thrombin particles with a loading of $MnO_2$ at 6.25 µg/mg particle (-▓-: fresh particle and -☐-: lyophilized particle) and at 0.0625 µg/mg particle (-▓-); -▲-: Cumulative release profile of thrombin from PLGA particles. The particles were incubated in PBS dissolved with $H_2O_2$ (0.2 mM $H_2O_2$). (B) The release rate of thrombin versus the hydraulic pressure difference (ΔP) between inside and outside of the lyophilized PLGA/$MnO_2$/thrombin particles (-☐-), fresh PLGA/$MnO_2$/thrombin particles (-▓-), and PLGA/thrombin particles (-▲-). In (A), data points and error bars represent the average and standard deviation of three different samples per condition, respectively. (C-1) Confocal image of PLGA/$MnO_2$ particles loaded with rhodamine-labeled $MnO_2$ nanosheets. In PBS, $MnO_2$ nanosheets were distributed uniformly in the particle. In contrast, particles incubated in 0.2 mM $H_2O_2$ solution showed the localization of rhodamine-labeled $MnO_2$ nanosheets to the particle wall, due to $O_2$-induced pressurization (C-2). Scale bars represent 3 µm. The mass of $MnO_2$ in the 1 mg of PLGA/$MnO_2$ particles was kept constant at 6.25 µg.

The ability of thrombin-encapsulating PLGA and PLGA/MnO$_2$ particles to release thrombin cargos was evaluated by measuring the mass of thrombin discharged from the particles (FIG. 4A). The particles were incubated in neutral PBS with 0.2 mM H$_2$O$_2$. The 0.2 mM concentration was chosen because it is sufficient to trigger the active release of thrombin without damaging particles. The H$_2$O$_2$ level also falls in the range of the physiological concentration of H$_2$O$_2$. Thrombin molecules burst out within the first hour. Thrombin molecules partially embedded in the surface layer of the particles contribute mainly to this initial burst. During 7 hours, fresh PLGA/MnO$_2$ particles, in which 6.25 µg of MnO$_2$ nanosheets were loaded into 1 mg of particles, released three times more thrombin than PLGA particles. Lyophilized PLGA/MnO$_2$ particles released thrombin faster than fresh particles. In contrast, PLGA/MnO$_2$ particles, in which 62 ng of MnO$_2$ nanosheets were loaded in 1 mg of particles, released thrombin cargos with a similar profile to PLGA particles. Thus, PLGA/MnO$_2$ particles (1 mg) encapsulated with 6.25 µg MnO$_2$ nanosheets were used in the rest of the study.

The H$_2$O$_2$-responsive release of thrombin is attributed to the generation of oxygen that increases the internal pressure of particles. The total flux of thrombin across PLGA particles (J$_s$) after the initial burst (1-20 hour) was correlated to the pressure difference between inside and outside particles (ΔP). The ΔP value of particle was calculated for each group using the ideal gas law for O$_2$ gas. The mass of O$_2$ shown in FIG. 12 was used in the calculation. (Calculation of ΔP is shown below). The calculated ΔP values for lyophilized and fresh PLGA/MnO$_2$ were 10.3 mmHg and 9.8 mmHg, respectively. In contrast, PLGA particles free of MnO$_2$ only exhibited a minimal pressure difference of 2.1 mmHg (Table 3). As shown in FIG. 4B, the release rate (J$_s$) of thrombin molecules was linearly related to the calculated ΔP.

Theoretical calculation of the difference between internal pressure and external pressure of PLGA/MnO$_2$ particles Radius of the PLGA shell: r=1.6 µm
Radius of the PLGA core: r=1.5 µm
Density of PLGA polymer: ρ=1.25 g/ml
Mass per PLGA shell:

$$M_{PLGA} = \rho \times \frac{4}{3}\pi\left[(1.6 \ \mu m)^3 - (1.5 \ \mu m)^3\right] = 3.77 \times 10^{-12}$$

g per particle
Number (N) of particles per 10 mg of PLGA polymer:
$N_{particle}$=10 mg/M$_{PLGA}$=2.65×10$^9$
Total volume of 10 mg PLGA particle:

$$V = N_{particle} \times \frac{4}{3}\pi(1.6 \ \mu m)^3 = 45.44 \ \mu L$$

Mole of O$_2$ gas generated inside the PLGA particle immersed in 100 µM H$_2$O$_2$ solution:

$$n_{O_2} = \frac{1}{2} \times$$

(initial $H_2O_2$ concentration−final $H_2O_2$ concentration)×$H_2O_2$ volume

Pressure change due to $O_2$ generation:

$$P_{O_2}V = n_{O_2}RT = P_{O_2} \times 45.44 \ \mu L = n_{O_2} \times 0.08206 \ \text{atm} \cdot \text{Lmol}^{-1}\text{K}^{-1} \times 310 \ \text{K}$$

$$\Delta P = \Delta P_{O_2} \Delta P_{H_2O} \approx \Delta P_{O_2} = P_{O_2} - 0 = P_{O_2}$$

TABLE 3

$O_2$ generation and the pressure change during $H_2O_2$ decomposition.

| Group | Initial $H_2O_2$ concentration (μM) | Final $H_2O_2$ concentration (μM) | Generated $O_2$ (nmol) | ΔP (mmHg) |
|---|---|---|---|---|
| Lyophilized PLGA/$MnO_2$ | 200 | 152 | 24 | 10.3 |
| Fresh PLGA/$MnO_2$ | 200 | 154 | 23 | 9.8 |
| PLGA w/o $MnO_2$ | 200 | 195 | 2.5 | 2.1 |

The linear dependence of $J_s$ on ΔP confirms that enhanced release of thrombin cargos from PLGA/MnO2/thrombin particles is primarily due to the ΔP, which is well-described by the Kedem-Katchalsky equation. The equation relates $J_s$ to the flux driven by the hydraulic pressure difference and that induced by the diffusion as shown in Eq. (2).

$$J_s = \alpha \Delta c + b \Delta P \quad (2)$$

Where $a = RT[\omega - \sigma(1-\sigma)\bar{c}L_p]$ and $b = (1-\sigma)\bar{c}L_p$ are constant values, Δc is the concentration difference of thrombin between particle interior and exterior, and ΔP is the hydraulic pressure difference between inside and outside of the particle. R represents the gas constant, T the temperature, and $\bar{c}$ is the average concentration of thrombin across the particle. $L_p$, ω, and σ are transport coefficients of filtration, solute permeability, and reflection coefficients of PLGA particle, respectively. In equation (2), Δc was approximated as a constant, equal to the concentration of thrombin inside the particle because the concentration of thrombin within the particle was several orders of magnitude higher than that outside the particle. Thus, $J_s$ becomes primarily dependent on ΔP.

To confirm the $O_2$-induced release of particles, the spatial distribution of fluorescently-labeled $MnO_2$ nanosheets in the PLGA/$MnO_2$ particles upon exposure to $H_2O_2$ was examined using confocal microscopy (FIG. 4C). $MnO_2$ nanosheets were distributed uniformly within the particle suspended in PBS. In contrast, the particles incubated in the PBS supplemented with 0.2 mM $H_2O_2$ displayed the localization of $MnO_2$ nanosheets to the particle wall. This result indicates that PLGA/$MnO_2$ particles increase the internal pressure due to the oxygen generation. Most of the $MnO_2$ nanosheets remained in the particles during $H_2O_2$-triggered thrombin release, as confirmed by the lack of change in the red fluorescence over time (FIG. 17).

Example 5. Microstructural Analysis of Fibrin Gel Formation

The extent to which the $H_2O_2$-mediated thrombin release rate modulates the fibrin gel formation was examined by visualizing the fibrous network formation process (FIGS. 5A and 5B). 72 ng of thrombin was encapsulated into 1 mg of PLGA or PLGA/$MnO_2$ particles. The loading amount of $MnO_2$ nanosheets was kept constant at 6.25 μg per mg of particles. The particles were mixed with an aqueous mixture of fluorescently-labeled fibrinogen and $H_2O_2$. The concentration of $H_2O_2$ in the fibrinogen solution was kept constant at 0.2 mM.

Figure 5:
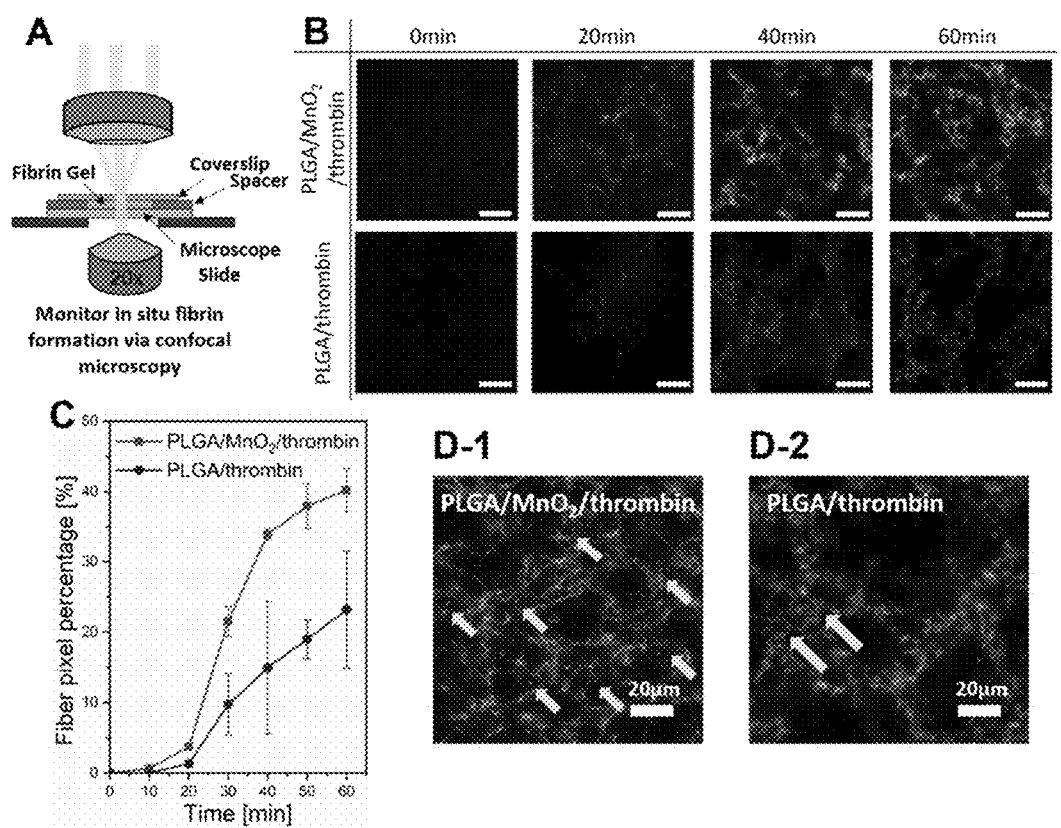
FIG. 5 shows image analysis of fibrin network formation modulated by PLGA/$MnO_2$/thrombin or PLGA/thrombin particles. (A) Schematic illustration of the experimental set-up to monitor fibrin formation in situ using confocal microscopy. (B) Confocal microscopy images of the fibrin fiber network formation over time. Fibrin was labeled with fluorescein. The fibrin gel was formed by mixing fibrinogen solution, 0.2 mM $H_2O_2$ solution, and PLGA/$MnO_2$/thrombin or PLGA/thrombin particles. The concentration of the $H_2O_2$ solution in the final mixture was kept constant at 0.2 mM. Scale bars represent 30 µm. (C) Quantification of the fibrin fiber pixel increased over time. Data points and error bars represent the average value and the standard deviation of three different samples per condition, respectively. (D1-D2) Confocal microscopy image of the fibrin networks (green color) and particles used to release thrombin (red color). (D-1) Fibrin networks formed using the PLGA/$MnO_2$/thrombin particles. (D-2) Fibrin networks formed using the PLGA/thrombin particles. In this study, the mass of $MnO_2$ and thrombin in the 1 mg of PLGA/$MnO_2$/thrombin particles were kept constant at 6.25 µg and 72 ng, respectively. The mass of thrombin in the 1 mg of PLGA/thrombin particles was kept constant at 72 ng. The mass ratio between fibrinogen and particles was kept constant at 1:4.

According to the real-time confocal images, thrombin-encapsulating PLGA/$MnO_2$ particles (PLGA/$MnO_2$/thrombin particles) served to form fibrin networks more rapidly than thrombin-encapsulating PLGA particles (PLGA/thrombin particles) (FIG. 5B). The quantitative image analysis conducted by counting the fibrin fibers disclosed that PLGA/$MnO_2$/thrombin particles increased the total number of fibrin fibers by a factor of two (FIG. 5C). PLGA/$MnO_2$/thrombin particles associated with the fibrin network, while PLGA/thrombin particles clustered together (FIGS. 5D-1 and D-2). The aggregation of PLGA/thrombin particles in the fibrin gel likely results from the hydrophobic interaction between the particles that do not associate with fibrin fibers.

Figure 6:
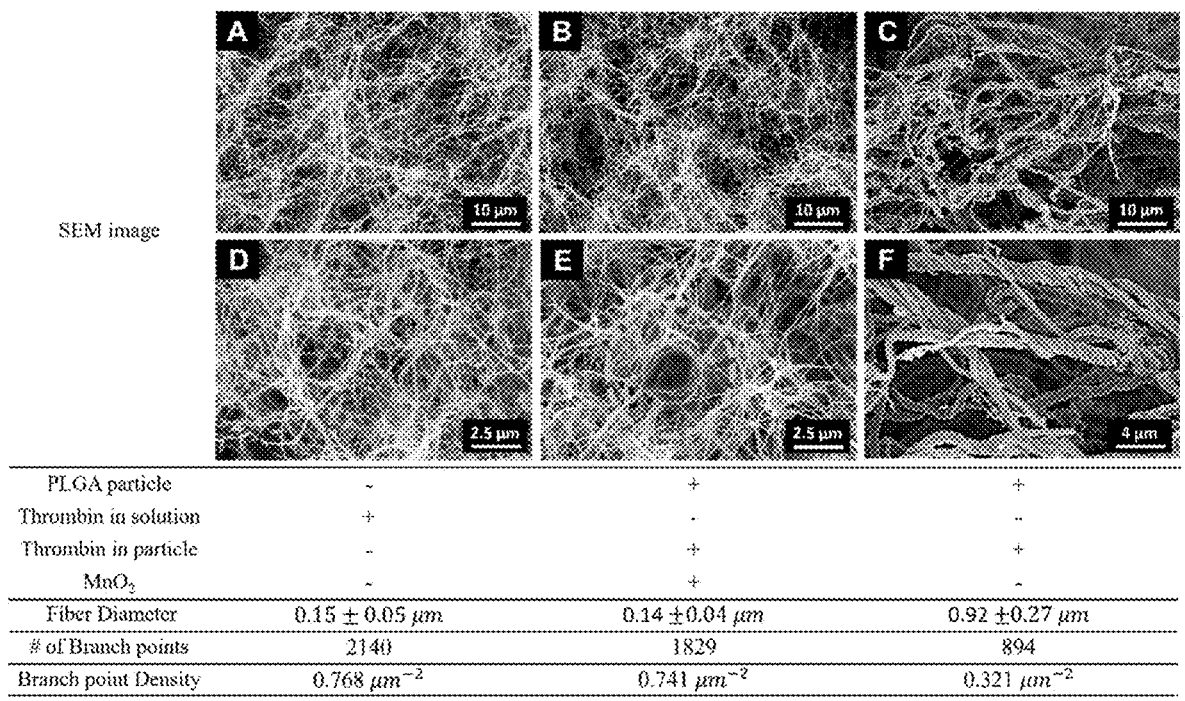
FIG. 6 shows analysis of the microstructure of the fibrin gel captured using SEM. (A & D) The fibrin gel formed by mixing fibrinogen (2.5 mg/mL) and thrombin (0.25 IU/mL). (B & E) The fibrin gel formed by mixing PLGA/$MnO_2$/thrombin particles (10 mg/mL), fibrinogen solution (2.5 mg/mL), and $H_2O_2$ (0.2 mM). 6.25 µg of $MnO_2$ nanosheets were loaded in the 1 mg of PLGA/$MnO_2$ particles. (C & F) The fibrin gel formed by mixing PLGA/thrombin particles (10 mg/mL), fibrinogen solution (2.5 mg/mL), and $H_2O_2$ (0.2 mM). The fiber diameter, number of branching points, and branching point density were noted in the table under corresponding images. In this study, the mass of thrombin in the 1 mg of particles was kept constant at 72 ng.

According to the SEM images of the gel, PLGA/$MnO_2$/thrombin particles resulted in the fibrin gel with similar microstructure to the gel made using the thrombin solution, as evaluated with the fiber diameter and the number and density of branching points (FIG. 6). In addition, PLGA/$MnO_2$/thrombin particles were connected with multiple fibrin fibers (FIG. 6E). In contrast, the fibrin gel formed by PLGA/thrombin particles (FIGS. 6C and 6F) showed a thicker fibrin fiber and a smaller number of branching points than two other conditions. (FIG. 6F).

PLGA/$MnO_2$/thrombin particles appear to release thrombin rapidly to increase the fibrinogen cleavage rate, compared with PLGA/thrombin particles. The resulting fibrinogen monomers serve to increase the number of branching points of fibrin networks instead of promoting longitudinal and lateral growth. In addition, the anchorage of fibrin fibers to PLGA/$MnO_2$/thrombin particles suggests that thrombin released from the particles activate the polymerization of fibrinogen on the particle surface and promote the sprouting of fibrin fibers (FIG. 6E). In contrast, PLGA/thrombin particles cleave fibrinopeptide at a lower rate than PLGA/$MnO_2$/thrombin particles due to the slow release of thrombin. As a consequence, fibrinogen monomers tend to polymerize into long fibers and then associate laterally to form thick fibers, as shown in FIG. 6F.

Figure 7:
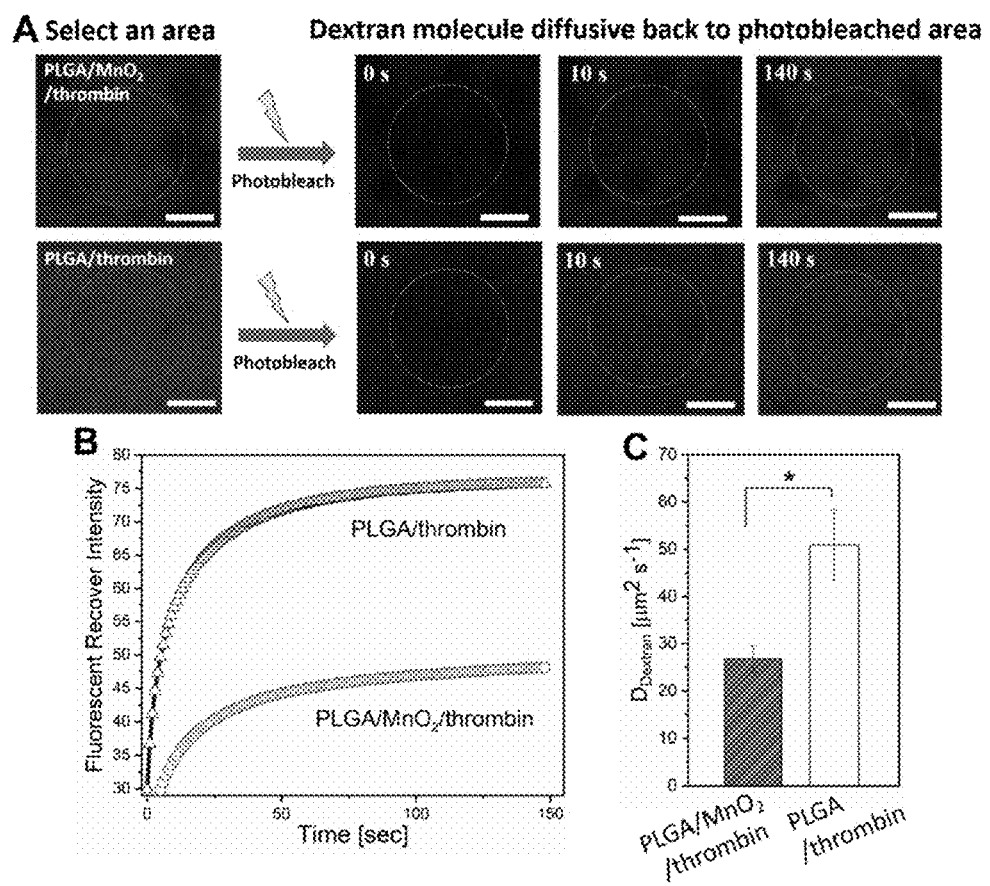
FIG. 7 shows FRAP analysis of dextran probes in fibrin gels made using PLGA/$MnO_2$/thrombin or PLGA/thrombin particles. (A) Confocal microscopy image of the fibrin gel that undergoes fluorescence recovery after photobleaching. The images were used to quantify the diffusion coefficient of the fluorescently labeled dextran (green color, $D_{dextran}$). The scale bar represents 10 µm. (B) Quantified fluorescent intensity of the dextran molecule in the photobleached area over time. (C) Quantification of $D_{dextran}$ in the fibrin gel. Data points and error bars represent the average and standard deviation of three different samples per condition, respectively. The composition of the particles used in this study was same as the condition in FIG. 4. * represents the statistical significance of the difference in the values between the two indicated groups (*$p<0.05$).

Permeability of the gel was examined by measuring a diffusion coefficient of dextran within the gel (FIGS. 7A and 7B). Dextran probes labeled with fluorescein were loaded into the fibrin gel for the FRAP assay. The diffusion coefficient of dextran was calculated from the fluorescence recovery rate in the photobleached spot. The fibrin gel prepared with PLGA/$MnO_2$/thrombin particles decreased the diffusion coefficient of the dextran by a factor of two compared with PLGA/thrombin particles (FIG. 7C).

The bio-adhesion of the fibrin gel to tissue was evaluated by filling the wound-mimicking hole introduced in a porcine skin explant with the gel (FIG. 18). Then, infiltration of fibrin networks to the skin tissue was observed using SEM. The gels prepared using the PLGA/$MnO_2$/thrombin particle and PLGA/thrombin particles anchored to the skin explant similar to the gel prepared with a mixture of fibrinogen and thrombin. The surface hydrophilicity of the gels was characterized by measuring the water contact angle. The thrombin released from PLGA particles did not alter the water contact angle on the fibrin gel surface significantly compared with the thrombin solution mixed with fibrinogen solution (FIG. 19).

Example 6. Rheological Characterization of Fibrin Gel Formation

One major advantage of using PLGA/MnO2/thrombin particle-based microgelator in the preparation of fibrin gels is to broaden the time window for gel preparation without reducing gel rigidity. This process is different from the conventional preparation method of the fibrin gel in which fibrinogen solution is mixed with the thrombin solution or powders. Branching points of the fibrin gel are responsible for the elastic response of the gel. The gelation process was monitored by measuring the storage modulus of the gel over time (FIG. 8A). Notably, mixing fibrinogen with the thrombin solution increased the storage modulus to 180 Pa within 5 minutes, with no significant increase after 5 minutes (FIG. 8B-1). Mixing fibrinogen, thrombin, and blank PLGA particles exhibited a limited increase in the storage modulus to 3 Pa. This result implies that blank PLGA particles that are not releasing thrombin molecules do not participate in forming the gel network. Instead, blank PLGA particles act as a physical barrier of the fibrin gel formation.

Figure 2:
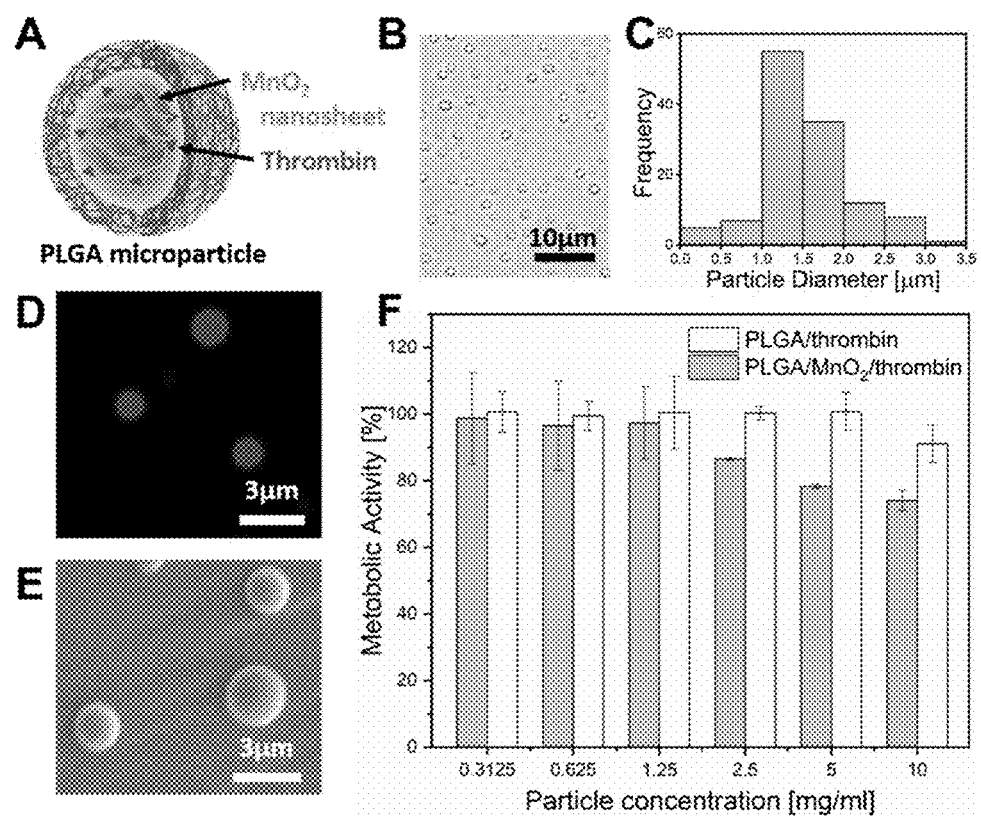
FIG. 2 shows characterization of PLGA/$MnO_2$/thrombin microparticles. (A) Schematic illustration of PLGA/$MnO_2$/ thrombin particles. (B) Optical microscopic image of PLGA/$MnO_2$/thrombin particles. (C) The size distribution of microparticles analyzed with optical microscope images. (D) Confocal image of PLGA/$MnO_2$/thrombin microparticles. $MnO_2$ nanosheets were labeled with red-colored rhodamine. (E) SEM image of PLGA/$MnO_2$/thrombin particles. (F) Quantification of the metabolic activity of C166 endothelial cells after incubation with PLGA or PLGA/ $MnO_2$ particles over 24 hours. PLGA/$MnO_2$ particles used herein are assembled by loading 6.25 µg of $MnO_2$ nanosheets in 1 mg of particles. In (F), data points and error bars represent the average values and standard deviation of three samples, respectively.

In the presence of $H_2O_2$, catalytic PLGA/MnO$_2$/thrombin particles served to increase the storage modulus of the gel continuously over 100 minutes. The storage modulus eventually reached approximately 250 Pa after 2.5 hours. In contrast, non-catalytic PLGA/thrombin particles led to a softer network than PLGA/MnO$_2$ particles, as indicated by the lower storage modulus throughout the measurements (FIG. 8B-2). The storage modulus at 3.75 hours after initiation of gelation was quantified as the equilibrium storage modulus, denoted as $G'_{eq}$, because no significant increase occurred beyond this time. The equilibrium storage modulus of the gel formed by mixing thrombin solution with fibrinogen was defined as the storage modulus at 25 minutes after initiation of gelation. $G'_{eq}$ of the gel prepared by the PLGA/MnO$_2$/thrombin particles was 33% higher than the fibrin gel prepared by mixing fibrinogen and thrombin solution, 71% higher than that of the fibrin gel prepared with the PLGA/thrombin particles, and 350% higher than that of the fibrin gel prepared by mixing fibrinogen, thrombin, and blank PLGA (FIG. 8C). The difference between these conditions is likely attributed to the short half-life of thrombin. In particular, the PLGA/MnO$_2$/thrombin particles serve to release biologically active thrombin and create reactive sites of fibrinogen to polymerize continuously, while the thrombin dissolved in solution loses bioactivity quickly. Furthermore, due to the connection of particles with interconnected fibrin fibers, the equilibrium storage moduli of the gel formed by thrombin releasing particles (e.g., PLGA/MnO$_2$/thrombin particles and PLGA/thrombin particles) are significantly higher than the storage modulus of the fibrin gel made with a mixture of fibrinogen, thrombin and blank PLGA particles.

In parallel, the time required to reach a stiffness equal to one half of $G'_{eq}$, denoted $t_{1/2}$, was quantified to assess the time window required for gel fabrication (FIG. 8D). While the $t_{1/2}$ of PLGA/MnO$_2$/thrombin particles was five times larger than the mixture of fibrinogen and thrombin, $t_{1/2}$ was significantly smaller than that attained with the PLGA/thrombin particles. The difference in $t_{1/2}$ between PLGA/MnO$_2$/thrombin and PLGA/thrombin particles is in accordance with the thrombin release and kinetic study, where the faster release of thrombin leads to smaller $t_{1/2}$. $t_{1/2}$ for the mixture of fibrinogen, thrombin, and PLGA particles was comparable to that with the PLGA/thrombin particles. This result indicates that the fibrin gelation process can be modulated by tuning the thrombin release profile from the particles. The accelerated release of thrombin from the PLGA/MnO$_2$/thrombin particles led to a decrease in the gelation time. A further increase in particle concentration will likely facilitate the gelation process due to the increase in total mass of thrombin in the pre-gelled fibrinogen solution. However, excess particles can act as physical barriers for the growth of fibrin fibers, which is implicated in FIG. 8C.

Storage modulus-time curves in FIG. 8B were fitted to a simple model proposed for a blood coagulation process (Eq. (3)),[44]

$$G'(t)=G'_{eq} \exp(-\beta/t) \quad (3)$$

in which $G'_{eq}$ represents the equilibrium storage modulus, $\beta$ is the characteristic time, and t indicates the time scale of gelation (FIG. 20). This single exponential model gave a good fitting quality ($R^2=0.994$) for the gelation process (Table 1). PLGA/MnO$_2$/thrombin particles resulted in the five-fold increase in $\beta$ compared with the mixture of fibrinogen and thrombin solutions where the smaller $\beta$ represents faster gelation. The PLGA/MnO$_2$/thrombin particles led to the smaller $\beta$ than PLGA/thrombin particles. However, the relatively low $R^2$ value with PLGA/MnO$_2$/thrombin particles (i.e., 0.93) indicates that the single exponential model may not sufficiently describe the gelation caused by the microparticles.

|  | $G'_{eq}$ [Pa] | $\beta$ [min] | $R^2$ |
|---|---|---|---|
| Thrombin solution | 208.3 | 2.858 | 0.994 |
| PLGA/MnO$_2$ particles loaded with thrombin | 246.6 | 15.99 | 0.9379 |
| PLGA particles loaded with thrombin | 149.7 | 19.6 | 0.9791 |
| Mixture of thrombin and blank PLGA particles | 6.96 | 16.42 | 0.9773 |

Table 1. Gelation curve fitting parameters obtained from the gelation curves in FIGS. 8B-1 and B-2 using equations (1). $G_{eq}'$ represents the final equilibrium storage modulus, and $\beta$ is the characteristic time for gelation.

Figure 8:
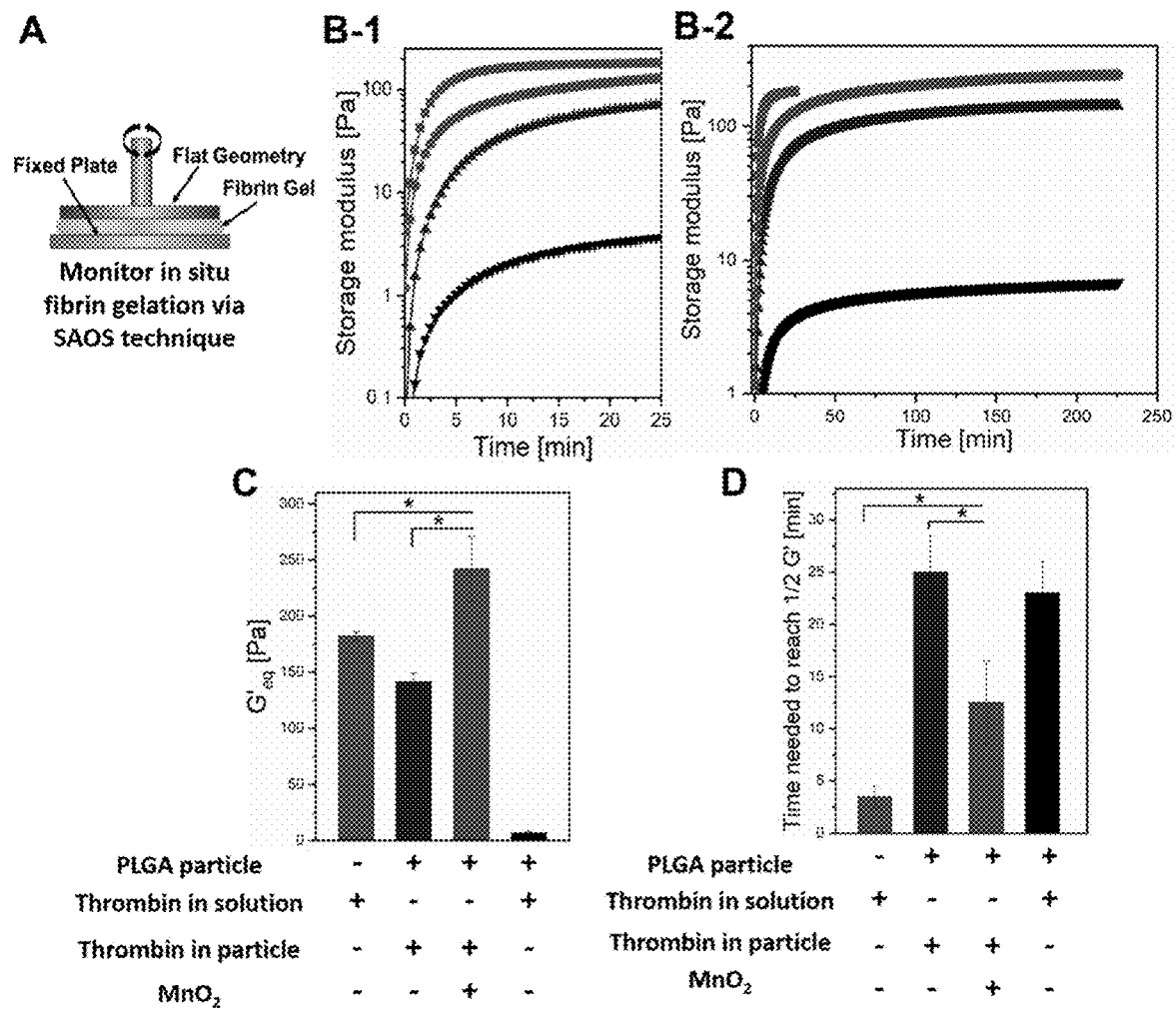
FIG. 8 shows rheological characterization of the fibrin gel formation. (A) Schematic illustration of the experimental set-up used to monitor changes in the storage modulus of the fibrin gel. (B-1) The initial increase in the storage modulus of the fibrin gel formed by mixing the fibrinogen solution with a thrombin solution (400 ng/mL) (-✳-), PLGA/$MnO_2$/thrombin particles (-✳-), PLGA/thrombin particles (-▲-), or a mixture of thrombin (400 ng/mL) and blank PLGA microparticle (-▼-). The analyses were focused on the first 25 minutes and (B-2) 250 minutes. (C) Final equilibrium storage modulus (left Y-axis) and (D) time need to reach ½ of equilibrium elastic modulus of the fibrin gel formed by conditions noted on the x-axis of the plot. In (C) and (D), data points and error bars represent the average and the standard deviation of three different samples per condition, respectively. The composition of the particles used in this study was same as the condition in FIG. 4. The mass ratio between fibrinogen and particles was kept constant at 1:3.3. For all conditions, the fibrinogen concentration was kept constant at a final concentration of 12 mg/mL. * represents the statistical significance of the difference in the values between the two indicated groups (*$p<0.05$).

Therefore, the evolution of the storage modulus was decomposed into two reaction phases. The first phase corresponds to the elastic response caused mainly by the polymerization and branching of fibrin fibers, while the other represents the elastic response associated with the lateral association of fibrin polymers. As shown in FIG. 8, the storage modulus increases more steeply during the first phase. To separate the distinct contributions, we exploited the double exponential model[45] (Eq. (4)), $$G'(t) = G'_0 + G'_1\left(1 - \exp\left(-\frac{t}{\tau_1}\right)\right) + G'_2\left(1 - \exp\left(-\frac{t}{\tau_2}\right)\right) \quad (4)$$

in which $G'_0$ is the storage modulus of the pre-gelled solutions, $G'_1$ is the storage modulus contributed by the first branching and crosslinking reaction phase, $G'_2$ is the storage modulus caused by the second lateral growth of fibrin polymers, and $1/\tau_1$ and $1/\tau_2$ are the characteristic rates for branching and lateral growth, respectively (FIG. 21).

As shown in Table 2, PLGA/MnO$_2$/thrombin particles showed slower rates of branching ($1/\tau_1$) and lateral growth ($1/\tau_2$) than the mixture of fibrinogen and thrombin by one and two orders of magnitude, respectively. Combined with the higher $G'_1$ and $G'_2$ values, this result confirms the advantages of using PLGA/MnO$_2$/thrombin particles to form a stiffer network while expanding the time window for gelation. In addition, PLGA/MnO$_2$/thrombin particles led to a faster branching rate ($1/\tau_1$) than PLGA/thrombin particles due to the faster release of thrombin molecules. The rate of lateral growth ($1/\tau_2$) had no significant difference. This result suggests that thrombin released from PLGA/MnO$_2$ particles mainly contributes to increasing the number of branching points of fibrin networks.

|  | $G'_1$ [Pa] | $1/\tau_1$ [1/min] | $G'_2$ [Pa] | $1/\tau_2$ [1/min] | $R^2$ |
| --- | --- | --- | --- | --- | --- |
| Thrombin solution | 65.35 | 0.195 | 118.4 | 0.195 | 0.9833 |
| PLGA/MnO$_2$/thrombin particles | 107.4 | 0.099 | 152.3 | 0.0097 | 0.9995 |
| PLGA/thrombin particles | 72.63 | 0.052 | 80.87 | 0.0089 | 0.9985 |
| Mixture of thrombin and blank PLGA particles | 4.34 | 0.052 | 3.642 | 0.005 | 0.9994 |

Table 2. Gelation curve fitting parameters obtained from the gelation curves in FIGS. 8B-1 and B-2 using equations (2). $G'_1$ is the storage modulus contributed by the branching and crosslinking reaction phase, $G'_2$ represents the storage modulus result from the second lateral growth of fibrin fibers, and $1/\tau_1$ and $1/\tau_2$ are the characteristic rate for branching and lateral growth, respectively.

Next it was determined whether the fibrin gel formed using the PLGA/MnO$_2$/thrombin particles modulate activities of endothelial cells to form blood vessel-like lumens similar to the gel formed using the thrombin solution. In this study, we loaded human umbilical vein endothelial cells (HUVECs) within fibrin gels of interests installed in the center channel ② of a microfluidic chip assembled for neovascularization study (FIG. 22). As the vascular endothelial growth factors (VEGF) diffuse from the outer channels ① and ③ to the HUVEC-laden fibrin gel, cells assembled to form interconnected endothelial lumens. Likely due to the similar fibrous structure between two fibrin gel systems, the length and the number of resulting endothelial lumens were similar to each other.

Example 6 Rheological Characterization of Blood Clotting Promoted by PLGA/MnO$_2$/Thrombin Particles The efficacy of PLGA/MnO$_2$/thrombin microparticles to activate the blood clotting in response to H$_2$O$_2$ was evaluated. In this study, 3.2% buffered sodium citrate was added to porcine blood to prevent instantaneous clotting after blood collection. The PLGA/MnO$_2$/thrombin particles were mixed with H$_2$O$_2$ solution (0.2 mM) to activate the release of thrombin cargos. Then, the particles were added to the blood. The blood mixed with the PLGA/MnO$_2$/thrombin particles formed a clot within 10 minutes. Therefore, the mixture stayed at the top of the tube after flipping. In contrast, the blood mixed with PLGA/thrombin particles failed to form a clot even after 30 minutes (FIG. 9A).

In parallel, the strengthened network of the blood mixture was monitored via SAOS rheology. The blood mixed with PLGA/MnO$_2$/thrombin particles displayed a continuous increase of the storage modulus up to 10 Pa through 70 minutes. (FIG. 9B). The storage modulus of the resulting blood clot was twice as large as that of the blood clot formed by thrombin solution (FIG. 9C and FIG. 23). In contrast, the blood mixed with PLGA/thrombin particles showed almost no increase in the storage modulus. This result indicated that PLGA/MnO$_2$/thrombin particles were able to discharge promptly and polymerize fibrinogen in the blood even with the presence of sodium citrate.

Figure 9:
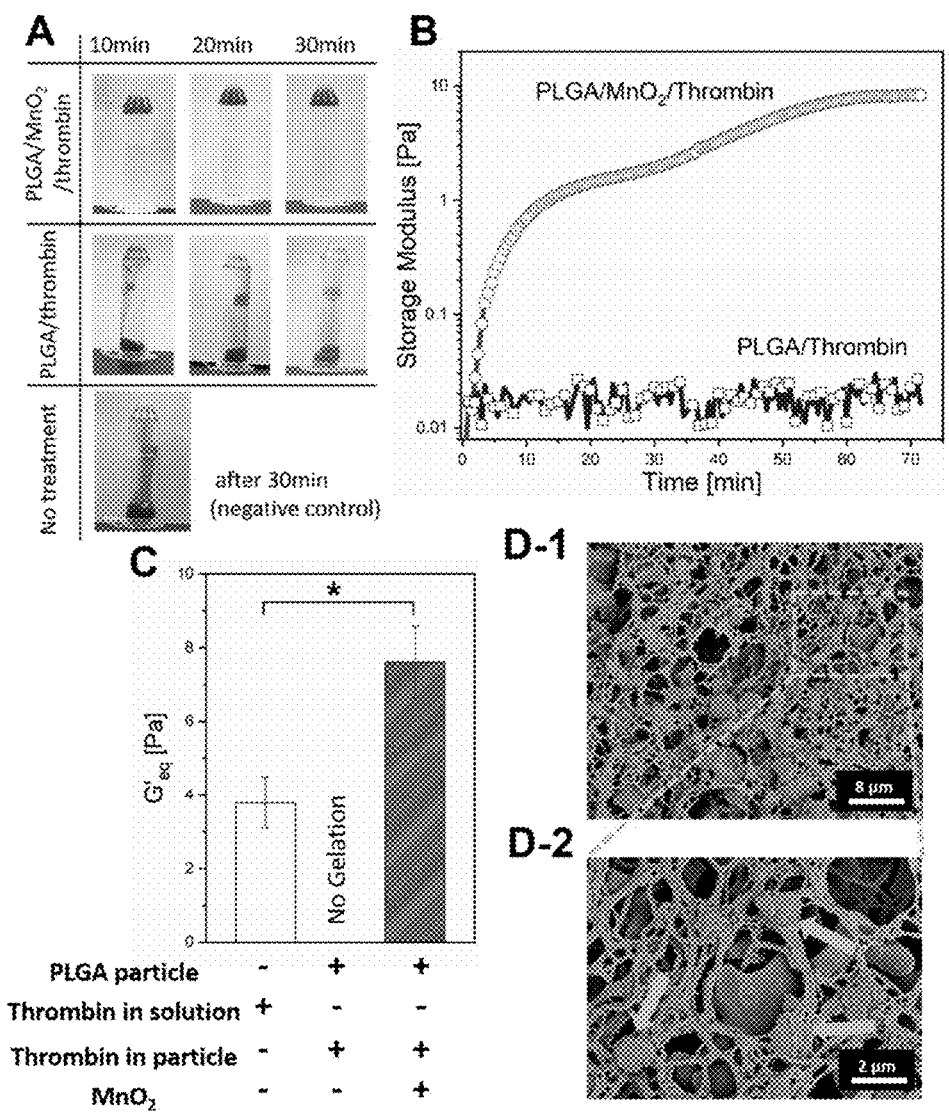
FIG. 9 shows analysis of the blood clot formation triggered by PLGA/$MnO_2$/thrombin particles. (A) Visual characterization of the clotting of porcine blood mixed by PLGA/$MnO_2$/thrombin or PLGA/thrombin microparticles. The blood mixture was placed in the tube and flipped every ten minutes. (B) Change in the storage modulus of the blood mixed with PLGA/$MnO_2$/thrombin particles (-○-) and PLGA/thrombin particles (-□-). (C) The equilibrium storage modulus ($G'_{eq}$) of the blood mixed with thrombin solution (400 ng/mL), PLGA/$MnO_2$/thrombin particles, or PLGA/thrombin particles. (D-1 to D-2) SEM images of a porcine blood clot formed by PLGA/$MnO_2$/thrombin particles. Yellow arrows locate the PLGA particles connected with fibrin fibers. (D-2) is a magnified view of the squared section in (D-1). Data points and error bars represent the average and standard deviation of three different samples per condition, respectively. The composition of the particles used in this study was the same as the condition in FIG. 4. The mass ratio between blood and particles was kept constant at 1:3.3. * represents the statistical significance of the difference in the values between the two indicated groups (*$p<0.05$).

The microstructure of the blood clot formed by PLGA/MnO$_2$/thrombin particles was observed with SEM (FIG. 9D). The images show an interconnected and highly branched fibrous network, similar to the pure fibrin gel prepared with PLGA/MnO$_2$/thrombin particles. The magnified image shown in FIG. 9D-2 confirms that PLGA/MnO$_2$ particles are connected with fibrin fibers likely because the polymerization of fibrinogen occurred actively on the particle surface (yellow arrows in FIG. 9D-2).

A catalytic microgelator can reproduce two major hemostasis processes: platelet-fiber association and thrombin-activated fibrin network formation. As such, a catalytic microgelator can be used as a hemostatic agent. Success in recapitulating the hemostasis process relies on the ability to expedite the discharge of thrombin cargos from microparticles. Otherwise, the microparticles fail to form the desired fibrin networks promptly, as demonstrated with PLGA particles loaded with thrombin only. In contrast, the catalytic microgelators exposed to H$_2$O$_2$ discharge thrombin actively into the blood and, in turn, promote fibrin network formation. In addition, as exhibited with SEM images and the mechanical test, PLGA/MnO$_2$/thrombin particles associated with fibrin fibers serve to stiffen the blood clot.

Example 7 In Vivo Hemostatic Performance Analysis

Figure 10:
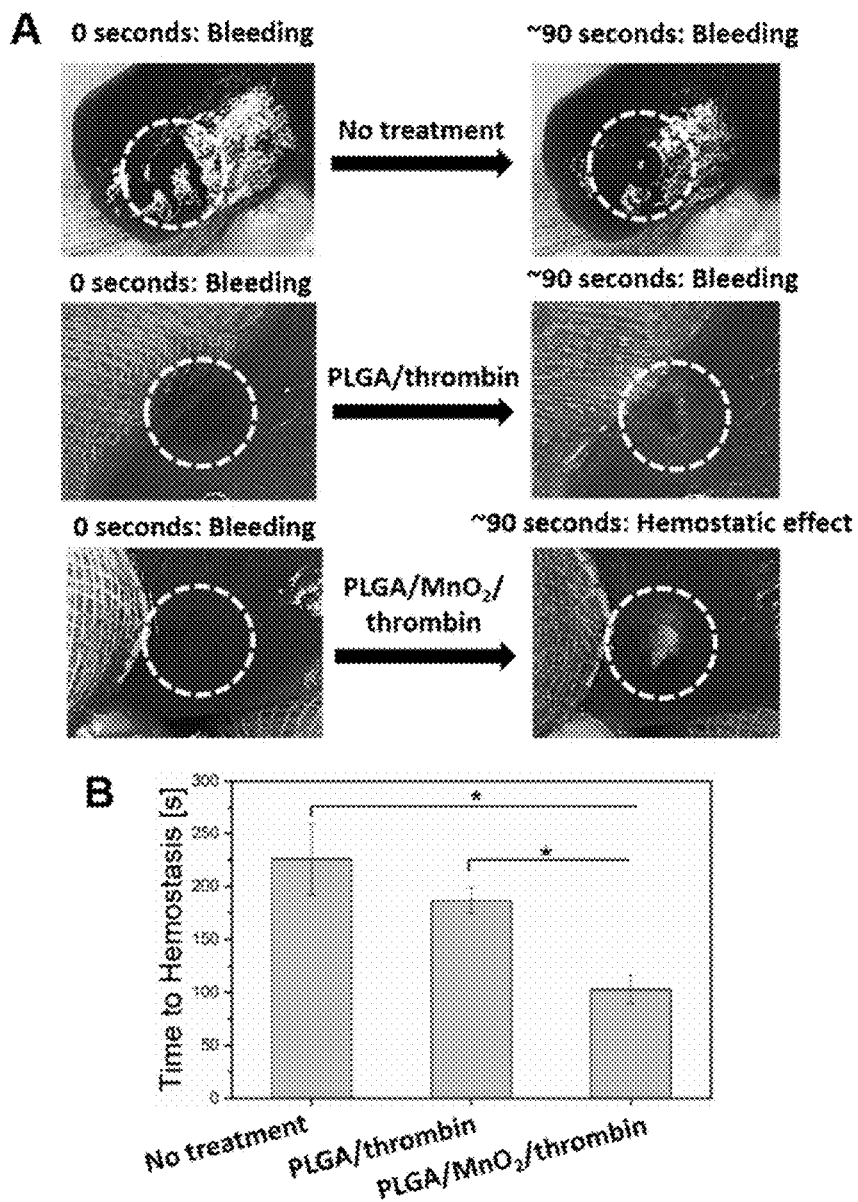
FIG. 10 shows the hemostatic capability of the PLGA/$MnO_2$/thrombin and PLGA/thrombin particles. (A) Photo images for the hemostatic effect within 90 seconds: control group without treatment (top), defect treated with PLGA/thrombin particles (middle), and defect treated with PLGA/$MnO_2$/thrombin particles (bottom). (B) Time to hemostasis in a bleeding rabbit liver treated with PLGA/$MnO_2$/thrombin and PLGA/thrombin particles. Data points and error bars represent the average and standard deviation of three different samples per condition, respectively. The particle concentration used in this study was the same as the condition in the in vitro bleeding control study. * represents the statistical significance of the difference in the values between the two indicated groups (*$p<0.05$).

The extent to which PLGA/MnO$_2$/thrombin particles can act as a hemostatic agent was examined by measuring time to hemostasis with a rabbit liver bleeding model (FIG. 10). Briefly, a 3 mm-diameter defect was created on the rabbit liver using a biopsy punch, and time to hemostasis was measured. The bleeding stopped after 225 seconds without any treatment. The repeated administration of PLGA/thrombin particles into the defect minimally influenced the bleeding. (FIG. 10A). After 90 seconds, the degree of bleeding was not significantly different from the untreated condition (FIG. 10A). Following continued administration of PLGA/thrombin particles, the bleeding stopped after 187 seconds. During this period, 50 drops of particle suspension were administered to the bleeding site. The insignificant difference of the time to hemostasis between these two groups indicated that the slow release of thrombin from the PLGA/thrombin particle is not sufficient to facilitate hemostasis. In contrast, the PLGA/MnO$_2$/thrombin particles mixed with 0.2 mM H$_2$O$_2$ solution at a concentration of 40 mg/ml could stop bleeding after 90 seconds (FIGS. 10A & B). During this period, ten drops of particle suspension were used to control bleeding. This accelerated hemostasis is attributed to the active release of thrombin triggered by H$_2$O$_2$.

The results of these studies demonstrate that a catalytic microgelator made of PLGA particles, $MnO_2$ nanosheets, and thrombin cargos is advantageous to extending gelation time and increasing mechanical strength of fibrin gels and blood clots. PLGA/$MnO_2$/thrombin particles suspended in media or blood containing 0.2 mM $H_2O_2$ took up and decomposed $H_2O_2$, generated $O_2$ gas, increased internal pressure, and finally ejected thrombin cargos much faster than PLGA/thrombin microparticles. The fibrinogen solution or blood mixed with PLGA/$MnO_2$/thrombin particles displayed the extended gelation time by one order of magnitude. Also, the mixture formed a more rigid and elastic fibrin network or blood clots than the gel formed by mixing thrombin and fibrinogen solution. These results are attributed to the PLGA/$MnO_2$/thrombin particles that serve to sustain the presence of thrombin molecules in the fibrinogen solution or blood. Thrombin released from PLGA/$MnO_2$ particles also promotes polymerization of fibrinogen on the particle surface and, in turn, increases the number of linkages between fibrin fibers and particles. As a consequence, PLGA/$MnO_2$ particles also act as reinforcing fillers.

We claim:

1. A composition comprising a core containing a (i) catalyst for decomposition of hydrogen peroxide ($H_2O_2$) and (ii) thrombin, wherein the catalyst for the decomposition of hydrogen peroxide is manganese oxide ($MnO_2$) particles or nanosheets, platinum (Pt), CuO (copper II oxide) particles or nanosheets, zinc peroxide ($ZnO_2$) particles or nanosheets, or catalase, and a polymer shell, wherein the catalyst for the decomposition of hydrogen peroxide ($H_2O_2$) and thrombin are located within the polymer shell.

2. The composition of claim 1, wherein the composition is lyophilized.

3. The composition of claim 1, wherein the polymer is a biodegradable polymer.

4. The composition of claim 1, wherein 1 mg of the composition comprises about 1 µg to about 20 µg of catalyst for the decomposition of $H_2O_2$ and about 25 ng to about 150 ng of thrombin.

5. A method of clotting blood or a blood product containing fibrinogen comprising:
   (a) adding $H_2O_2$ to the composition of claim 1 to form a mixture and adding the mixture to the blood or blood product;
   (b) adding $H_2O_2$ to the blood or blood product to form a mixture and adding the composition of claim 1 to the mixture; or
   (c) adding $H_2O_2$ and the composition of claim 1 to the blood or blood product to form a mixture.

6. The method of claim 5, wherein fibrinogen is additionally added to the blood or blood product or to any of the mixtures of (a), (b), or (c).

7. A method of promoting blood clotting in a subject comprising adding $H_2O_2$ to the composition of claim 1 to form a mixture and then administering an effective amount of the mixture to the subject.

8. The method of claim 7, wherein fibrinogen is added to the mixture before administering the mixture to the subject.

9. The method of claim 7, wherein the subject has a coagulopathic condition or tissue defect and the method is effective for treating the coagulopathic condition or tissue defect in the subject.

10. The method of claim 9, wherein the tissue defect is an external wound, an internal wound, an ulcer, a burn, a natural defect, a surgical incision, or any combination thereof.

11. The method of claim 9, wherein the tissue defect is caused by traumatic injury, disease, infection, surgical intervention, natural causes, or any combinations thereof.

12. A method of making a gel comprising contacting the composition of claim 1 with a fibrinogen solution or powder and $H_2O_2$ to form a mixture and allowing the mixture to form a gel.

13. The method of claim 12, wherein the fibrinogen is present at about 0.5 mg/ml to about 5.0 mg/ml in the fibrinogen solution or mixture and the $H_2O_2$ is present at about 0.1 mM to about 0.6 mM.

14. The method of claim 12, further comprising adding one or more types of cells to the mixture so that the cells are present within the gel.

15. The method of claim 14, wherein the one or more types of cells are endothelial cells, fibroblast cells, tissue specific cells, or a combination thereof.

16. The method of claim 15, wherein the endothelial cells are adult vein endothelial cells, adult artery endothelial cells, embryonic stem cell-derived endothelial cells, iPS-derived endothelial cells, umbilical vein endothelial cells, umbilical artery endothelial cells, endothelial progenitor cells derived from bone marrow, endothelial progenitor cells derived from cord blood, endothelial progenitor cells derived from peripheral blood, endothelial progenitor cells derived from adipose tissues, or combinations thereof.

17. The method of claim 16, wherein the umbilical vein endothelial cells are human umbilical vein endothelial cells (HUVEC).

18. The method of claim 15, wherein the fibroblast cells are human foreskin fibroblasts, human embryonic fibroblasts, mouse embryonic fibroblasts, skin fibroblast cells, vascular fibroblast cells, myofibroblasts, smooth muscle cells, mesenchymal stem cells (MSCs)-derived fibroblast cells, or combinations thereof.

19. The method of claim 15, wherein the tissue-specific cells are muscle cells, pancreatic beta cells, osteoblasts, chondrocytes, myoblasts, adipocytes, neuronal cells, glial cells, cardiomyocytes, liver cells, urethral cells, kidney cells, periosteal cells, bladder cells, odontoblasts, dental pulp cells, periodontal cells, tenocytes, lung cells, cardiac cells, skeletal cells, stem cell, iPS cell derived tissue specific cells, or a combination thereof.

20. The method of claim 15, wherein the tissue specific cells are myoblasts, pancreatic beta-islet cells, cardiomyocytes, liver cells, lung cells, neural cells, bone cells, kidney cells, or combinations thereof.

21. A method of making catalytic microgelator particles comprising:
   (a) adding thrombin to a suspension of an $H_2O_2$ decomposition catalyst to form an internal aqueous phase mixture;
   (b) adding the internal aqueous phase mixture to an organic phase comprising a polymer in a solvent and mixing to form a first emulsion;
   (c) adding the first emulsion to an external aqueous phase solution comprising a water soluble polymer and mixing to prepare a second emulsion; and
   (d) collecting the resulting catalytic microgelator particles, which comprise a core containing the thrombin and the $H_2O_2$ decomposition catalyst located within a polymer shell.

22. A method of clotting blood or a blood product comprising adding the composition of claim 1 to the blood or blood product.

* * * * *